United States Patent
Li et al.

(10) Patent No.: US 9,698,359 B2
(45) Date of Patent: *Jul. 4, 2017

(54) SYNTHESIS OF PLATINUM AND PALLADIUM COMPLEXES AS NARROW-BAND PHOSPHORESCENT EMITTERS FOR FULL COLOR DISPLAYS

(71) Applicant: Arizona Board of Regents, Acting for and on Behalf of Arizona State University, Scottsdale, AZ (US)

(72) Inventors: Jian Li, Tempe, AZ (US); Eric Turner, Phoenix, AZ (US)

(73) Assignee: ARIZONA BOARD OF REGENTS, ACTING FOR AND ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/996,522

(22) Filed: Jan. 15, 2016

(65) Prior Publication Data

US 2016/0197291 A1    Jul. 7, 2016

Related U.S. Application Data

(62) Division of application No. 13/479,921, filed on May 24, 2012, now Pat. No. 9,238,668.

(60) Provisional application No. 61/490,111, filed on May 26, 2011.

(51) Int. Cl.
| | |
|---|---|
| C09K 11/06 | (2006.01) |
| C07F 15/00 | (2006.01) |
| H01L 51/50 | (2006.01) |
| H01L 51/00 | (2006.01) |

(52) U.S. Cl.
CPC ...... *H01L 51/0087* (2013.01); *C07F 15/0086* (2013.01); *C09K 11/06* (2013.01); *C09K 2211/1044* (2013.01); *C09K 2211/185* (2013.01); *H01L 51/5016* (2013.01)

(58) Field of Classification Search
CPC .................. C07F 15/00; H01L 51/50
USPC .............. 546/2; 313/504; 252/301.16
See application file for complete search history.

(56) References Cited

U.S. PATENT DOCUMENTS

| | | |
|---|---|---|
| 4,769,292 A | 9/1988 | Tang et al. |
| 5,707,745 A | 1/1998 | Forrest et al. |
| 5,844,363 A | 12/1998 | Gu et al. |
| 6,303,238 B1 | 10/2001 | Thompson et al. |
| 6,780,528 B2 | 8/2004 | Tsuboyama et al. |
| 7,002,013 B1 | 2/2006 | Chi et al. |
| 7,037,599 B2 | 5/2006 | Culligan et al. |
| 7,279,704 B2 | 10/2007 | Walters et al. |
| 7,332,232 B2 | 2/2008 | Ma et al. |
| 7,442,797 B2 | 10/2008 | Itoh et al. |
| 7,501,190 B2 | 3/2009 | Ise |
| 7,655,322 B2 | 2/2010 | Forrest et al. |
| 7,947,383 B2 | 5/2011 | Ise et al. |
| 8,389,725 B2 | 3/2013 | Li et al. |
| 8,617,723 B2 | 12/2013 | Stoessel |
| 8,816,080 B2 | 8/2014 | Li et al. |
| 8,871,361 B2 | 10/2014 | Xia et al. |
| 8,927,713 B2 | 1/2015 | Li et al. |
| 8,946,417 B2 | 2/2015 | Jian et al. |
| 9,059,412 B2 | 6/2015 | Zeng et al. |
| 9,224,963 B2 | 12/2015 | Li et al. |
| 9,238,668 B2 | 1/2016 | Li et al. |
| 9,312,505 B2 | 4/2016 | Brooks et al. |
| 9,324,957 B2 | 4/2016 | Li et al. |
| 9,382,273 B2 | 7/2016 | Li et al. |
| 9,385,329 B2 | 7/2016 | Li et al. |
| 9,425,415 B2 | 8/2016 | Li et al. |
| 9,550,801 B2 | 1/2017 | Li |
| 2002/0068190 A1 | 6/2002 | Tsuboyama et al. |
| 2003/0062519 A1 | 4/2003 | Yamazaki et al. |
| 2005/0170207 A1 | 8/2005 | Ma et al. |
| 2005/0260446 A1 | 11/2005 | Mackenzie et al. |
| 2006/0073359 A1 | 4/2006 | Ise et al. |
| 2006/0094875 A1 | 5/2006 | Itoh et al. |
| 2006/0202197 A1 | 9/2006 | Nakayama et al. |
| 2006/0210831 A1 | 9/2006 | Sano et al. |
| 2006/0263635 A1 | 11/2006 | Ise |
| 2006/0286406 A1 | 12/2006 | Igarashi et al. |
| 2007/0057630 A1 | 3/2007 | Nishita et al. |
| 2007/0059551 A1 | 3/2007 | Yamazaki |
| 2007/0082284 A1 | 4/2007 | Stoessel et al. |
| 2007/0103060 A1 | 5/2007 | Itoh et al. |
| 2008/0001530 A1 | 1/2008 | Ise et al. |
| 2008/0036373 A1 | 2/2008 | Itoh et al. |
| 2008/0054799 A1 | 3/2008 | Satou |
| 2008/0079358 A1 | 4/2008 | Satou |

(Continued)

FOREIGN PATENT DOCUMENTS

| | | |
|---|---|---|
| CN | 1777663 | 5/2006 |
| CN | 1894269 | 1/2007 |

(Continued)

OTHER PUBLICATIONS

Wong; Challenges in organometallic research—Great opportunity for solar cells and OLEDs, Journal of Organometallic Chemistry, 2009, 694, 2644-2647.

(Continued)

*Primary Examiner* — Charanjit Aulakh

(74) *Attorney, Agent, or Firm* — Fish & Richardson P.C.

(57) ABSTRACT

Platinum and palladium complexes are disclosed that can be useful as narrow band phosphorescent emitters. Also disclosed are methods for preparing and using the platinum and palladium complexes.

21 Claims, 2 Drawing Sheets

(56) References Cited

U.S. PATENT DOCUMENTS

| | | |
|---|---|---|
| 2008/0241518 A1 | 10/2008 | Satou et al. |
| 2008/0241589 A1 | 10/2008 | Fukunaga et al. |
| 2009/0026936 A1 | 1/2009 | Satou et al. |
| 2009/0026939 A1 | 1/2009 | Kinoshita et al. |
| 2009/0032989 A1 | 2/2009 | Karim et al. |
| 2009/0039768 A1 | 2/2009 | Igarashi et al. |
| 2009/0079340 A1 | 3/2009 | Kinoshita et al. |
| 2009/0128008 A1 | 5/2009 | Ise et al. |
| 2009/0218561 A1 | 9/2009 | Kitamura et al. |
| 2009/0261721 A1 | 10/2009 | Murakami et al. |
| 2009/0267500 A1 | 10/2009 | Kinoshita et al. |
| 2010/0000606 A1 | 1/2010 | Thompson et al. |
| 2010/0013386 A1 | 1/2010 | Thompson et al. |
| 2010/0171111 A1 | 7/2010 | Takada et al. |
| 2010/0297522 A1 | 11/2010 | Creeth et al. |
| 2012/0095232 A1 | 4/2012 | Li et al. |
| 2012/0181528 A1 | 7/2012 | Takada et al. |
| 2012/0215001 A1 | 8/2012 | Li et al. |
| 2012/0223634 A1 | 9/2012 | Xia et al. |
| 2012/0302753 A1 | 11/2012 | Li |
| 2013/0048963 A1 | 2/2013 | Beers et al. |
| 2013/0168656 A1 | 7/2013 | Tsai et al. |
| 2013/0203996 A1 | 8/2013 | Li et al. |
| 2013/0237706 A1 | 9/2013 | Li |
| 2013/0341600 A1 | 12/2013 | Lin et al. |
| 2014/0014922 A1 | 1/2014 | Lin et al. |
| 2014/0027733 A1 | 1/2014 | Zeng et al. |
| 2014/0084261 A1 | 3/2014 | Brooks et al. |
| 2014/0114072 A1 | 4/2014 | Li et al. |
| 2014/0203248 A1 | 7/2014 | Zhou et al. |
| 2014/0330019 A1 | 11/2014 | Li et al. |
| 2014/0364605 A1 | 12/2014 | Li et al. |
| 2015/0008419 A1 | 1/2015 | Li |
| 2015/0028323 A1 | 1/2015 | Xia et al. |
| 2015/0069334 A1 | 3/2015 | Xia et al. |
| 2015/0105556 A1 | 4/2015 | Li et al. |
| 2015/0162552 A1 | 6/2015 | Li et al. |
| 2015/0194616 A1 | 7/2015 | Li et al. |
| 2015/0228914 A1 | 8/2015 | Li et al. |
| 2015/0287938 A1 | 10/2015 | Li et al. |
| 2015/0318500 A1 | 11/2015 | Li |
| 2015/0349279 A1 | 12/2015 | Li et al. |
| 2016/0028028 A1 | 1/2016 | Li et al. |
| 2016/0043331 A1 | 2/2016 | Li et al. |
| 2016/0133862 A1 | 5/2016 | Li et al. |
| 2016/0285015 A1 | 9/2016 | Li et al. |
| 2016/0359120 A1 | 12/2016 | Li |
| 2016/0359125 A1 | 12/2016 | Li et al. |
| 2017/0005278 A1 | 1/2017 | Li et al. |
| 2017/0012224 A1 | 1/2017 | Li et al. |

FOREIGN PATENT DOCUMENTS

| | | |
|---|---|---|
| CN | 101142223 | 3/2008 |
| CN | 101667626 | 3/2010 |
| CN | 102449108 A | 5/2012 |
| CN | 102892860 | 1/2013 |
| CN | 102971396 | 3/2013 |
| CN | 104232076 | 12/2014 |
| CN | 104693243 | 6/2015 |
| CN | 105367605 A1 | 3/2016 |
| CN | 105418591 A1 | 3/2016 |
| EP | 1808052 | 7/2007 |
| EP | 1874893 | 1/2008 |
| EP | 1874894 | 1/2008 |
| EP | 1919928 | 5/2008 |
| EP | 2036907 | 3/2009 |
| EP | 2096690 | 9/2009 |
| EP | 2417217 | 2/2012 |
| EP | 2112213 | 7/2012 |
| EP | 2711999 | 3/2014 |
| JP | 2005267557 | 9/2005 |
| JP | 2005310733 | 11/2005 |
| JP | 2006047240 | 2/2006 |
| JP | 2006232784 | 9/2006 |
| JP | 2006242080 | 9/2006 |
| JP | 2006242081 | 9/2006 |
| JP | 2006256999 | 9/2006 |
| JP | 2006257238 | 9/2006 |
| JP | 2006261623 | 9/2006 |
| JP | 2006290988 | 10/2006 |
| JP | 2006313796 | 11/2006 |
| JP | 2006332622 | 12/2006 |
| JP | 2006351638 | 12/2006 |
| JP | 2007019462 | 1/2007 |
| JP | 2007042875 | 2/2007 |
| JP | 2007053132 | 3/2007 |
| JP | 2007066581 | 3/2007 |
| JP | 2007073620 | 3/2007 |
| JP | 2007073845 | 3/2007 |
| JP | 2007073900 | 3/2007 |
| JP | 2007080593 | 3/2007 |
| JP | 2007080677 | 3/2007 |
| JP | 2007088105 | 4/2007 |
| JP | 2007088164 | 4/2007 |
| JP | 2007096259 | 4/2007 |
| JP | 2007110067 | 4/2007 |
| JP | 2007110102 | 4/2007 |
| JP | 2007258550 | 10/2007 |
| JP | 2007324309 | 12/2007 |
| JP | 2008010353 | 1/2008 |
| JP | 2008091860 | 4/2008 |
| JP | 2008103535 | 5/2008 |
| JP | 2008108617 | 5/2008 |
| JP | 2008109085 | 5/2008 |
| JP | 2008109103 | 5/2008 |
| JP | 2008160087 | 7/2008 |
| JP | 2008198801 | 8/2008 |
| JP | 2008270729 | 11/2008 |
| JP | 2008270736 | 11/2008 |
| JP | 2009016184 | 1/2009 |
| JP | 2009016579 | 1/2009 |
| JP | 2009032977 | 2/2009 |
| JP | 2009032988 | 2/2009 |
| JP | 2009266943 | 11/2009 |
| JP | 2009267171 | 11/2009 |
| JP | 2009267244 | 11/2009 |
| JP | 2009272339 | 11/2009 |
| JP | 2009283891 | 12/2009 |
| JP | 2010135689 | 6/2010 |
| JP | 2012222255 | 11/2012 |
| JP | 2013525436 | 6/2013 |
| JP | 5604505 | 10/2014 |
| JP | 2014221807 | 11/2014 |
| JP | 2015081257 | 4/2015 |
| KR | 1020060115371 | 11/2006 |
| KR | 2007061830 | 6/2007 |
| KR | 2007112465 | 11/2007 |
| KR | 1020130043460 | 4/2013 |
| TW | 200701835 | 1/2007 |
| TW | 201307365 | 2/2013 |
| WO | WO0070655 | 11/2000 |
| WO | WO2004003108 A1 | 1/2004 |
| WO | WO2004108857 | 12/2004 |
| WO | WO2005042444 | 5/2005 |
| WO | WO2005042550 | 5/2005 |
| WO | WO2006033440 | 3/2006 |
| WO | WO2006098505 | 9/2006 |
| WO | WO2006115299 | 11/2006 |
| WO | WO2006115301 | 11/2006 |
| WO | WO2007034985 | 3/2007 |
| WO | WO2007069498 | 6/2007 |
| WO | WO2008066192 | 6/2008 |
| WO | WO2008066195 | 6/2008 |
| WO | WO2008066196 | 6/2008 |
| WO | WO2008117889 | 10/2008 |
| WO | WO2008123540 | 10/2008 |
| WO | WO2009017211 | 2/2009 |
| WO | WO2010118026 | 10/2010 |
| WO | WO2011137429 | 11/2011 |
| WO | WO2011137431 | 11/2011 |
| WO | WO2012112853 | 8/2012 |
| WO | WO2012142387 | 10/2012 |
| WO | WO2012162488 | 11/2012 |

(56) References Cited

FOREIGN PATENT DOCUMENTS

| WO | WO2012163471 | 12/2012 |
| WO | WO2013130483 | 9/2013 |
| WO | WO2014016611 A1 | 1/2014 |
| WO | WO2014031977 | 2/2014 |
| WO | WO2014047616 | 3/2014 |
| WO | WO2014109814 | 7/2014 |
| WO | WO2015027060 | 2/2015 |
| WO | WO2015131158 | 9/2015 |
| WO | WO2016025921 | 2/2016 |
| WO | WO2016029186 | 2/2016 |

OTHER PUBLICATIONS

JP2009267244, English Translation from EPO, Nov. 2009, 80 pages.
JP2010135689, English translation from EPO, Jun. 2010, 95 pages.
Chi et al.; Transition-metal phosphors with cyclometalating ligands: fundamentals and applications, Chemical Society Reviews, vol. 39, No. 2, Feb. 2010, pp. 638-655.
Satake et al., "Interconvertible Cationic and Neutral Pyridinylimidazole η3-Allylpalladium Complexes. Structural Assignment by 1H, 13C, and 15N NMR and X-ray Diffraction", Organometallics, vol. 18, No. 24, 1999, pp. 5108-5111.
International Preliminary Report on Patentability issued on Nov. 26, 2013 for Intl. Pat. App. No. PCT/US2012/039323 filed May 24, 2012 and published as WO 2012/162488 on Nov. 29, 2012 (Applicants—Arizona Board of Regents Acting for and on Behalf of Arizona State University; Inventors—Li et al.; (7 pages).
International Search Report mailed on Aug. 17, 2012 for Intl. Pat. App. No. PCT/US2012/039323 filed May 24, 2012 and published as WO 2012/162488 on Nov. 29, 2012 (Applicants—Arizona Board of Regents Acting for and on Behalf of Arizona State University; Inventors—Li et al.; (2 pages).
Written Opinion mailed on Aug. 17, 2012 for Intl. Pat. App. No. PCT/US2012/039323 filed May 24, 2012 and published as WO 2012/162488 on Nov. 29, 2012 (Applicants—Arizona Board of Regents Acting for and on Behalf of Arizona State University; Inventors—Li et al.; (6 pages).
Baldo et al., "Highly Efficient Phosphorescent Emission from Organic Electroluminescent Devices," Nature, vol. 395, Sep. 10, 1998, pp. 151-154.
Baldo et al., "Very high-efficiency green organic light-emitting devices based on electrophosphorescence," Applied Physics Letters, vol. 75, No. 1, Jul. 5, 1999, pp. 4-6.
Xiao-Chu Hang et al., "Highly Efficient Blue-Emitting Cyclometalated Platinum(II) Complexes by Judicious Molecular Design," Angewandte Chemie, International Edition, vol. 52, Issue 26, Jun. 24, 2013, pp. 6753-6756.
Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.
Barry O'Brien et al.: White organic light emitting diodes using Pt-based red, green and blue phosphorescent dopants. Proc. SPIE, vol. 8829, pp. 1-6, Aug. 25, 2013.
Ayan Maity et al., "Room-temperature synthesis of cyclometalated iridium(III) complexes; kinetic isomers and reactive functionalities" Chem. Sci., vol. 4, pp. 1175-1181 (2013).
Shiro Koseki et al., "Spin-orbit coupling analyses of the geometrical effects on phosphorescence in Ir(ppy)$_3$ and its derivatives", J. Phys. Chem. C, vol. 117, pp. 5314-5327 (2013).
Ji Hyun Seo et al., "Efficient blue-green organic light-emitting diodes based on heteroleptic tris-cyclometalated iridium (III) complexes". Thin Solid Films, vol. 517, pp. 1807-1810 (2009).
Vanessa Wood et al., "Colloidal quantum dot light-emitting devices," Nano Reviews, vol. 1, 2010, 8 pages.
Glauco Ponterini et al., "Comparison of Radiationless Decay Processes in Osmium and Platinum Porphyrins," J. Am. Chem. Soc., vol. 105, No. 14, 1983, pp. 4639-4645.
Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.
Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.
Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Evan L. Williams et al., "Excimer-Based White Phosphorescent Organic Light Emitting Diodes with Nearly 100% Internal Quantum Efficiency," Adv. Mater., vol. 19, 2007, pp. 197-202.
Shih-Chun Lo et al., "High-Triplet-Energy Dendrons: Enhancing the Luminescence of Deep Blue Phosphorescent Iridium(III) Complexes," J. Am. Chem. Soc., vol. 131, 2009, pp. 16681-16688.
Jan Kalinowski et al., "Light-emitting devices based on organometallic platinum complexes as emitters," Coordination Chemistry Reviews, vol. 255, 2011, pp. 2401-2425.
Ke Feng et al., "Norbornene-Based Copolymers Containing Platinum Complexes and Bis(carbazolyl)benzene Groups in Their Side-Chains," Macromolecules, vol. 42, 2009, pp. 6855-6864.
Chi-Ming Che et al., "Photophysical Properties and OLED Applications of Phosphorescent Platinum(II) Schiff Base Complexes," Chem. Eur. J., vol. 16, 2010, pp. 233-247.
Stephen R. Forrest, "The path to ubiquitous and low-cost organic electronic appliances on plastic," Nature, vol. 428, Apr. 29, 2004, pp. 911-918.
Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.
Xiaofan Ren et al., "Ultrahigh Energy Gap Hosts in Deep Blue Organic Electrophosphorescent Devices," Chem. Mater., vol. 16, 2004, pp. 4743-4747.
Jeonghun Kwak et al., "Bright and Efficient Full-Color Colloidal Quantum Dot Light-Emitting Diodes Using an Inverted Device Structure," Nano Lett., 2012, Vo. 12, pp. 2362-2366.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Eric Turner et al., "Cyclometalated Platinum Complexes with Luminescent Quantum Yields Approaching 100%," Inorg. Chem., 2013, vol. 52, pp. 7344-7351.
Steven C. F. Kui et al., "Robust Phosphorescent Platinum(II) Complexes Containing Tetradentate O O^N^C^N N O^N^C^N C O^N^C^N N Ligands: Excimeric Excited State and Application in Organic White-Light-Emitting Diodes," Chem. Eur. J., 2013, vol. 19, pp. 69-73.
Steven C. F. Kui et al., "Robust phosphorescent platinum(II) complexes with tetradentate O O^N^C^N N O^N^C^N C O^N^C^N N ligands: high efficiency OLEDs with excellent efficiency stability," Chem. Commun., 2013, vol. 49, pp. 1497-1499.
Guijie Li et al., "Efficient and stable red organic light emitting devices from a tetradentate cyclometalated platinum complex," Organic Electronics, 2014, vol. 15 pp. 1862-1867.
Guijie Li et al., Efficient and Stable White Organic Light-Emitting Diodes Employing a Single Emitter, Adv. Mater., 2014, vol. 26, pp. 2931-2936.
Barry O'Brien et al., "High efficiency white organic light emitting diodes employing blue and red platinum emitters," Journal of Photonics for Energy, vol. 4, 2014, pp. 043597-1-043597-8.
Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.
Tyler Fleetham et al., "Efficient "pure" blue OLEDs employing tetradentate Pt complexes with a narrow spectral bandwidth," Advanced Materials (Weinheim, Germany), Vo. 26, No. 41, 2014, pp. 7116-7121.

(56) References Cited

OTHER PUBLICATIONS

Murakami; JP 2007258550, English machine translation from EPO, Oct. 4, 2007. 80 pages.
Murakami; JP 2007324309, English machine translation from EPO, Dec. 13, 2007, 89 pages.
Dorwald; "Side Reactions in Organic Synthesis: A Guide to Successful Synthesis Design," Chapter 1, 2005 Wiley-VCH Verlag GmbH & Co. KGaA, Wienheim, 32 pages.
Office Action and Search Report for ROC (Taiwan) Patent Application No. 1011188250 dated Jan. 11, 2016, 8 pages.
Marc Lepeltier et al., "Efficient blue green organic light-emitting devices based on a monofluorinated heteroleptic Iridium(III) complex," Synthetic Metals, vol. 199, 2015, pp. 139-146.
Stefan Bernhard, "The First Six Years: A Report," Department of Chemistry, Princeton University, May 2008, 11 pages.

SYNTHESIS OF PLATINUM AND PALLADIUM COMPLEXES AS NARROW-BAND PHOSPHORESCENT EMITTERS FOR FULL COLOR DISPLAYS

CROSS-REFERENCE TO RELATED APPLICATIONS

This application is a divisional of U.S. application Ser. No. 13/479,921, filed May 24, 2012, which claims the benefit of U.S. Application No. 61/490,111, filed May 26, 2011, both of which are hereby incorporated by reference in their entirety.

STATEMENT OF GOVERNMENT SUPPORT

The present invention was made with financial support from the National Science Foundation under Career Grant No. 0748867. The U.S. government has certain rights in this invention.

BACKGROUND

Technical Field

The present disclosure relates to platinum and palladium complexes that can be useful as narrow band phosphorescent emitters in, for example, full color displays.

Technical Background

Compounds capable of absorbing and/or emitting light are ideally suited for use in a wide variety of applications, including optical and electro-optical devices, photo-absorbing devices, and as markers for bio-applications. Much research has been devoted to the discovery and optimization of organic and organometallic materials for use in such applications. Generally, research in this area aims to accomplish a number of goals, including improvements in absorption and emission efficiency, as well as improvements in processing ability, among others.

Despite significant advances in research devoted to optical, electro-optical, and marker materials, existing materials have a number disadvantages, including poor processing ability, inefficient emission or absorption, and less than ideal stability, among others. Thus, a need exists for new materials which exhibit improved performance in optical emitting and absorbing applications. This need and other needs are satisfied by the present invention.

SUMMARY

The present invention relates to platinum and palladium complexes that can be useful as narrow band phosphorescent emitters in, for example, full color displays. Such complexes are useful in organic-light-emitting-diodes (OLEDs).

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

In one aspect, the present invention provides a complex that can be represented by the general formula:

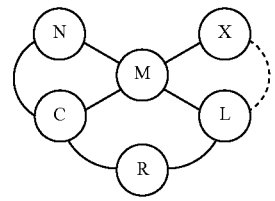

where (N^C) represents the emitting portion of the ligand, (L^X) represents an ancillary portion of the ligand, which may be linked, or not linked, M represents platinum or palladium, R represents a linking motif that connects (N^C) to (L^X) while disrupting the conjugation between them.

In one aspect, the excited state properties of the complex can be represented by the scheme:

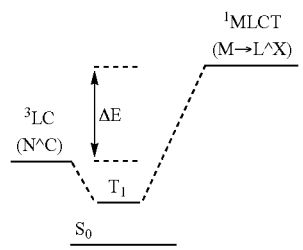

The energy of the ligand centered triplet state ($^3$LC), and the metal-to-ligand charge transfer state ($^1$MLCT) can be tuned independently. The nature of the emitting portion (N^C) drive the emission energy, as well as the width of the emission profile. The nature of the ancillary portion (L^X) is responsible for the enhancement or suppression of the vibronic progression in the emission profile, as well as the decay rates associated with emission. Control of both can yield complexes that emit narrowly at wavelengths useful for display applications.

In one aspect, the present invention provides a complex that can be represented by the formula:

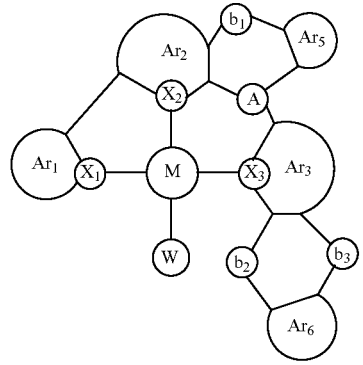

wherein M represents platinum, palladium, or a combination thereof, where each of $Ar_1$, $Ar_2$, and $Ar_3$ independently represent an aromatic ring or heterocyclic group which can be substituted or unsubstituted; wherein each of $X_1$, $X_2$ and $X_3$ can individually be coordinated to a platinum and/or palladium atom, and can independently represent a carbon or a nitrogen atom, wherein $Ar_5$ can represent an aromatic ring, a heterocyclic group, or a combination thereof, wherein $Ar_6$ can represent an aromatic ring, a heterocyclic group, a combination thereof, or can be absent; wherein W can be coordinated to a platinum or a palladium atom, and can be represented as a halogen atom, an aryl group, or a heteroaryl group which may be substituted bonded directly or through an oxygen atom, sulfur atom, nitrogen atom, or phosphorous atom; wherein A can represent a linking atom, such as, for example, nitrogen, carbon, boron, phosphorus, silicon, or a combination thereof, and wherein A can optionally be substituted, wherein each of $b_1$, $b_2$, and $b_3$ can individually optionally be present or absent, and if present can independently represent oxygen, sulfur, nitrogen, carbon, boron, phosphorus, silicon, or a combination thereof.

In another aspect, the present invention provides a complex that can be represented by the formula:

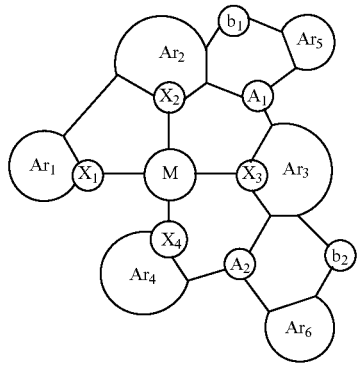

wherein M represents platinum, palladium, or a combination thereof, wherein each of $Ar_1$, $Ar_2$, $Ar_3$, and $Ar_4$ independently represent an aromatic ring or heterocyclic group which can be substituted or unsubstituted; where each of $X_1$, $X_2$, $X_3$ and $X_4$ can individually be coordinated to a platinum and/or palladium atom, and can independently represent a carbon and/or a nitrogen atom, wherein $Ar_5$ can represent an aromatic ring, a heterocyclic group, or a combination thereof, wherein $Ar_6$ can represent an aromatic ring, a heterocyclic group, a combination thereof, or can be absent; wherein each of $A_1$ and $A_2$ can independently represent a linking atom, such as, for example, nitrogen, carbon, boron, phosphorus, silicon, or a combination thereof, and wherein each of $A_1$ and $A_2$ can independently optionally be substituted, wherein each of $b_1$ and $b_2$ can individually optionally be present or absent, and if present can independently represent oxygen, sulfur, nitrogen, carbon, boron, phosphorus, silicon, or a combination thereof.

In still another aspect, the present invention provides a complex that can be represented by the formula:

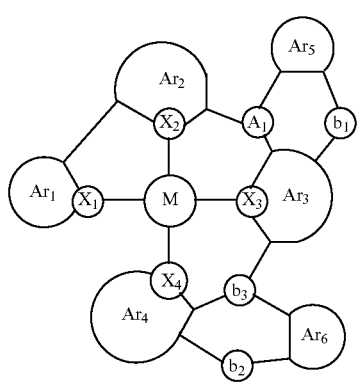

wherein M represents platinum, palladium, or a combination thereof, wherein each of $Ar_1$, $Ar_2$, $Ar_3$, and $Ar_4$ independently represent an aromatic ring or heterocyclic group which can be substituted or unsubstituted; wherein each of $X_1$, $X_2$, $X_3$ and $X_4$ can individually be coordinated to the platinum and/or palladium atom, and can independently represent a carbon and/or a nitrogen atom, wherein $Ar_5$ can represent an aromatic ring, a heterocyclic group, or a combination thereof, wherein $Ar_6$ can represent an aromatic ring, a heterocyclic group, a combination thereof, or can be absent; wherein $A_1$ can represent a linking atom, such as, for example, nitrogen, carbon, boron, phosphorus, silicon, or a combination thereof, and wherein $A_1$ can optionally be substituted, wherein each $b_1$, $b_2$, and $b_3$ can individually optionally be present or absent, and if present can independently represent oxygen, sulfur, nitrogen, carbon, boron, phosphorus, silicon, or a combination thereof.

Also disclosed are full color display devices comprising one or more of the platinum complexes described herein.

BRIEF DESCRIPTION OF THE FIGURES

The accompanying figures, which are incorporated in and constitute a part of this specification, illustrate several aspects and together with the description serve to explain the principles of the invention.

Figure 1:
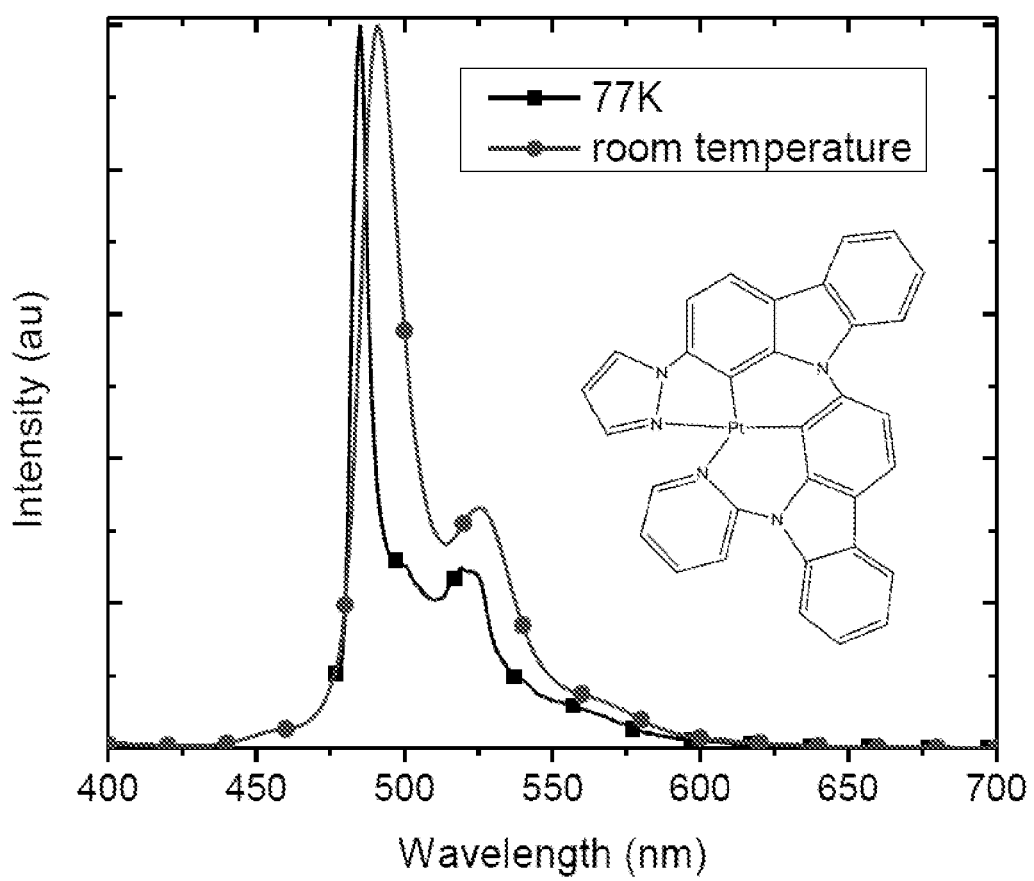
FIG. 1 illustrates an emission spectra of the compound Pt—N1N (inset) at 77K and room temperature, in accordance with various aspects of the present disclosure.
Figure 2:
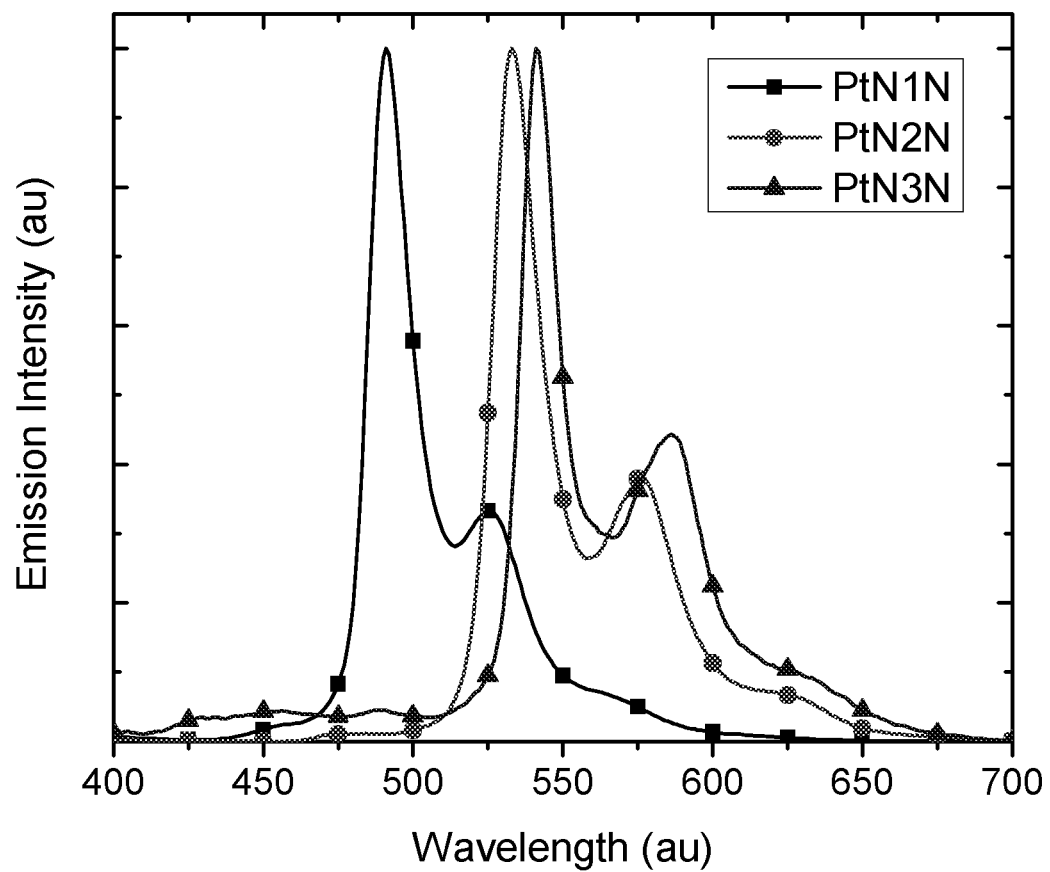
FIG. 2 illustrates the room temperature emission spectra of the compounds Pt—N1N, Pt—N2N, and Pt—N3N(inset), in accordance with various aspects of the present disclosure.
Figure 2:
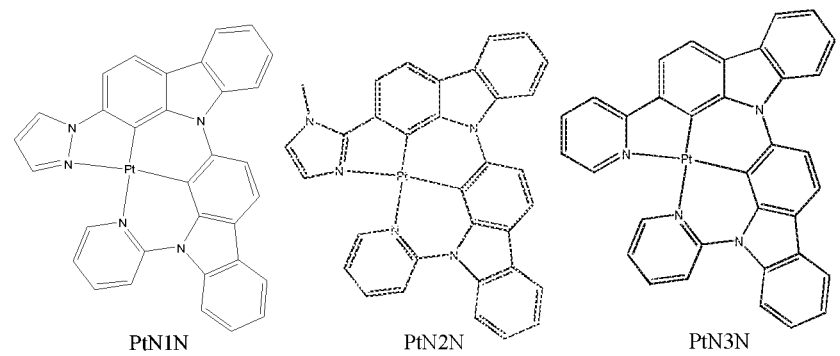

Additional aspects of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

The chemical names and structures disclosed herein can also comprise bonds stemming from those structures. For example, if

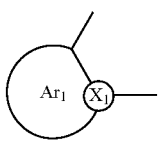

is pyridine, then the bonds from the

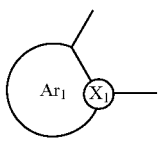

structure are included in the pyridine, thus, for example, $X_1$ can be either the nitrogen or a carbon in the pyridine that is bonded to another component of the complex, for example the M component.

As used in the specification and the appended claims, the singular forms "a," "an" and "the" include plural referents unless the context clearly dictates otherwise. Thus, for example, reference to "a component" includes mixtures of two or more components.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

The terms "amine" or "amino" as used herein are represented by the formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "nitrile" as used herein is represented by the formula —CN.

The term "thiol" as used herein is represented by the formula —SH.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

The term "heterocyclic" or the like terms refer to cyclic structures including a heteroatom. Thus, "heterocyclic" includes both aromatic and non-aromatic ring structures with one or more heteroatoms. Non-limiting examples of heterocyclic includes, pyridine, isoquinoline, methylpyrrole and thiophene etc.

As briefly described above, the present invention is directed to platinum and/or palladium complexes. In one aspect, the compositions disclosed here can provide emission spectra of platinum and/or palladium. In another aspect, the compositions disclosed herein can provide tunable emission spectra. In yet another aspect, the compositions disclosed herein can have an emission spectrum having a narrow bandwidth.

In one aspect, the inventive composition comprises a platinum (II) complex. In another aspect, the inventive composition comprises a palladium (II) complex.

For any of the structures recited herein, unless specifically stated to the contrary, various symbols and/or abbreviations are used wherein: M represents platinum, palladium, or a combination thereof, where each of $Ar_1$, $Ar_2$, $Ar_3$, and $Ar_4$, if present, independently represent an aromatic ring or heterocyclic group which can be substituted or unsubstituted; where each $X_n$ can be coordinated to a platinum and/or palladium atom, and can independently represent a carbon and/or a nitrogen atom, wherein $Ar_5$ can represent an aromatic ring, a heterocyclic group, or a combination thereof, where $Ar_6$ can represent an aromatic ring, a heterocyclic group, a combination thereof, or can be absent; where each $A_n$ can independently represent a linking atom, such as, for example, nitrogen, carbon, boron, phosphorus, silicon, or a combination thereof, and wherein each $A_n$ can optionally be substituted, where each $b_n$ can optionally be present or absent, and if present can independently represent oxygen, sulfur, nitrogen, carbon, boron, phosphorus, silicon, or a combination thereof.

Also, for any of the structures recited herein, $R_n$ can represent $R_1$-$R_{10}$, where each R can independently represent a hydrogen atom, an alkyl group, a haloalkyl group, an aralkyl group, an alkenyl group, an alkynyl group, an aryl group, an amino group, a mono- or di-alkylamino group, a mono- or diaryl amino group, an alkoxy group, an aryloxy group, a heteroaryloxy group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, an ureido group, a phosphoramide group, a hydroxyl group, amercapto group, a halogen atom, a cyano group, a sulfo group, a carboxyl group, a nitro group, a hydrzino group, a substituted silyl group, a polymerizable group, or a combination thereof; wherein if a plurality of R's are present (e.g., $R_n$), n can be from about 0 to about 4, and wherein each R can be the same or different from any other R, and wherein U, if present, can be oxygen, sulfur, or N—$R_n$. Also, designation of $R^1$, $R^2$, $R^3$ etc in the application relates to the definition of $R_n$. Thus, limited subset of $R^1$, $R^2$, $R^3$ etc recited in the application does not preclude other substituents defined as $R_n$ to also be included in that list.

In one aspect, the compositions of the present invention can be represented by the general formula:

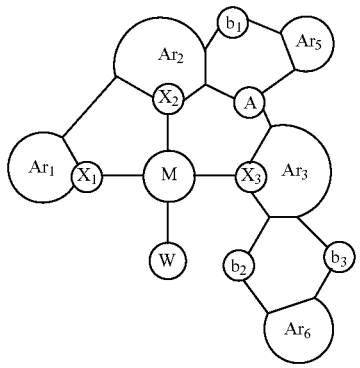

wherein M represents platinum, palladium, or a combination thereof, where each of $Ar_1$, $Ar_2$, and $Ar_3$ independently represent an aromatic ring or heterocyclic group which can be substituted or unsubstituted; wherein each of $X_1$, $X_2$ and $X_3$ can individually be coordinated to a platinum and/or palladium atom, and can independently represent a carbon or a nitrogen atom, wherein $Ar_5$ can represent an aromatic ring, a heterocyclic group, or a combination thereof, where $Ar_6$ can represent an aromatic ring, a heterocyclic group, a combination thereof, or can be absent; wherein W can be coordinated to a platinum or a palladium atom, and can be represented as a halogen atom, an aryl group, or a heteroaryl group which may be substituted bonded directly or through an oxygen atom, sulfur atom, nitrogen atom, or phosphorous atom; wherein A can represent a linking atom, such as, for example, nitrogen, carbon, boron, phosphorus, silicon, or a combination thereof, and wherein A can optionally be substituted, wherein each of $b_1$, $b_2$, and $b_3$ can individually optionally be present or absent, and if present can independently represent oxygen, sulfur, nitrogen, carbon, boron, phosphorus, silicon, or a combination thereof.

In one aspect, M can be Pt, such as Pt(II). In another aspect, M can be Pd, such as Pd(II).

In one aspect, W can be Cl or F. For example, W can be Cl. In another aspect, W can be $C_3$-$C_6$ alkynyl. For example, W can be $C_3$ alkynyl. In another aspect, W can be nitrile. In another aspect, W can be $C_6$-$C_{10}$ aryl. For example, W can be phenyl or naphthyl. The phenyl or naphthyl can be substituted or unsubstituted. For example, the phenyl can be unsubstituted. In another example, the phenyl can be alkyl substituted, such as $C_1$-$C_6$ alkyl substituted. In another aspect, the $C_6$-$C_{10}$ aryl can be bonded to M via an oxygen atom. In another aspect, W can be $C_5$-$C_9$ hetero aryl. For example, W can be isoquinoline. In another example, W can be quinazoline.

In one aspect,

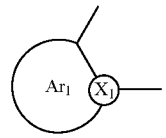

can be pyridine, quinazoline, isoquinoline, methylimidazole, or

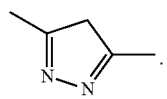

In one aspect,

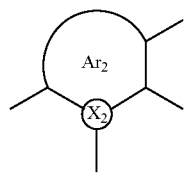

can be phenyl or pyridine.

In one aspect,

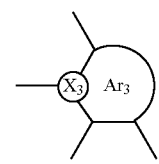

can be phenyl or pyridine.

In one aspect,

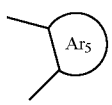

can be phenyl.

In one aspect,

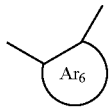

can be phenyl or can be absent. For example,

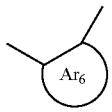

can be absent. In another example,

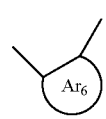

can be phenyl.

In one aspect,

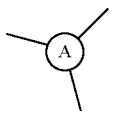

can be one or more of:

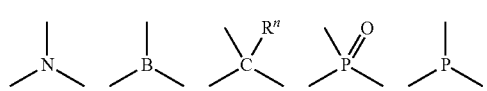

or a combination thereof. In one aspect, $R''$ can be $C_1$-$C_3$ alkyl. For example,

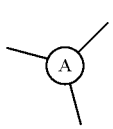 can be 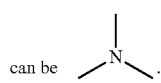.

In one aspect,

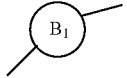

can be present or absent. For example,

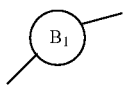

can be absent. If present,

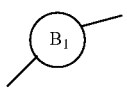

can, in one aspect, be —O—.

In one aspect,

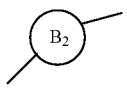

can be present or absent. For example,

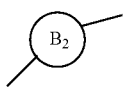

can be absent. In another example,

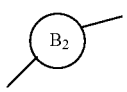

can be —S—, —S($R^1$)$_2$—, —C($R^2$)$_2$—, —O—, —NH— or —N$R''$—. In one aspect, each $R^1$ can individually be H or $C_1$-$C_3$ alkyl, for example $C_2$ alkyl. In one aspect, each $R^2$ can individually be H or $C_1$-$C_3$ alkyl, for example $C_1$ alkyl. In one aspect, $R''$ can be $C_1$-$C_3$ alkyl. For example, $R''$ can be $C_2$ alkyl.

In one aspect,

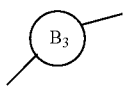

can be present or absent. For example,

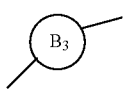

can be absent. In another example,

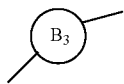

can be —S—, —S(R$^1$)$_2$—, —O—, —NH— or —NR"—. In one aspect, each R$^1$ can individually be H or C$_1$-C$_3$ alkyl, for example C$_2$ alkyl. In one aspect, R" can be C$_1$-C$_3$ alkyl. For example, R" can be C$_2$ alkyl.

In one aspect, W can be Cl, nitrile, phenyl, naphthyl or isoquinoline; and

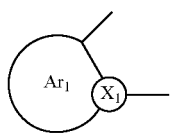

can be isoquinoline, methylimidazole, or

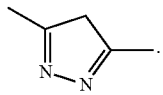

In another aspect, W can be Cl, nitrile, phenyl, naphthyl or isoquinoline;

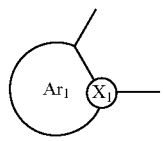

can be isoquinoline, methylimidazole, or

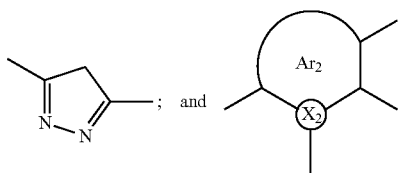

can be phenyl. In another aspect, W can be Cl, nitrile, phenyl, naphthyl or isoquinoline;

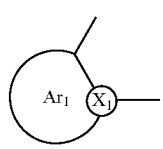

can be isoquinoline, methylimidazole, or

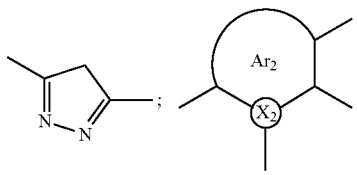

can be phenyl; and

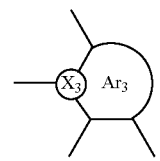

can be pyridine. In another aspect, W can be Cl, nitrile, phenyl, naphthyl or isoquinoline;

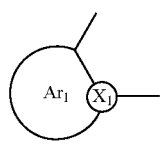

can be isoquinoline, methylimidazole, or

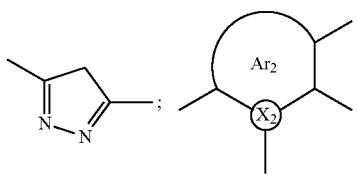

can be phenyl;

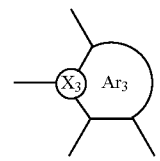

can be pyridine;

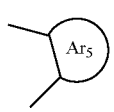

can be phenyl; and

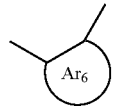

can be absent. In another aspect, W can be Cl, nitrile, phenyl, naphthyl or isoquinoline;

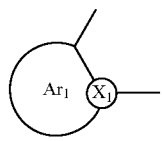

can be isoquinoline, methylimidazole, or

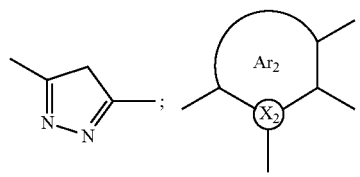

can be phenyl;

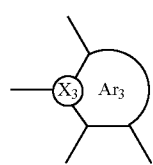

can be pyridine;

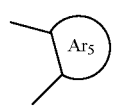

can be phenyl; and

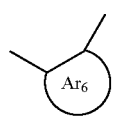

can be phenyl.

In another aspect, the compositions of the present invention can be represented by the general formula:

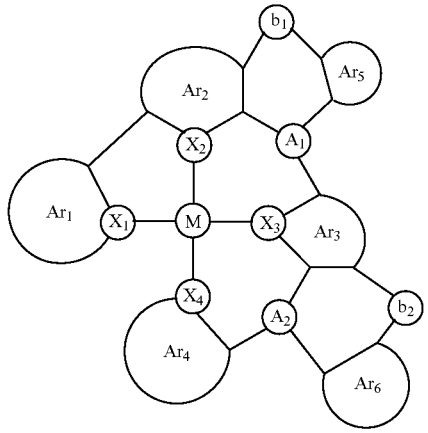

wherein M represents platinum, palladium, or a combination thereof, wherein each of $Ar_1$, $Ar_2$, $Ar_3$, and $Ar_4$ independently represent an aromatic ring or heterocyclic group which can be substituted or unsubstituted; where each of $X_1$, $X_2$, $X_3$ and $X_4$ can individually be coordinated to a platinum and/or palladium atom, and can independently represent a carbon and/or a nitrogen atom, wherein $Ar_5$ can represent an aromatic ring, a heterocyclic group, or a combination thereof, wherein $Ar_6$ can represent an aromatic ring, a heterocyclic group, a combination thereof, or can be absent; wherein each of $A_1$ and $A_2$ can independently represent a linking atom, such as, for example, nitrogen, carbon, boron, phosphorus, silicon, or a combination thereof, and wherein each of $A_1$ and $A_2$ can independently optionally be substituted, wherein each of $b_1$ and $b_2$ can individually optionally be present or absent, and if present can independently represent oxygen, sulfur, nitrogen, carbon, boron, phosphorus, silicon, or a combination thereof.

In one aspect, M can be Pt, such as Pt(II). In another aspect, M can be Pd, such as Pd(II).

In one aspect,

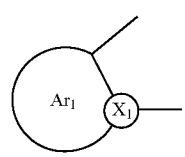

can be pyridine, quinazoline, isoquinoline, methylimidazole, or

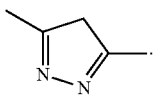

In one aspect,

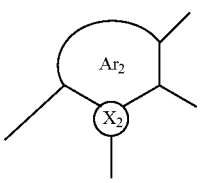

can be phenyl or pyridine.

In one aspect,
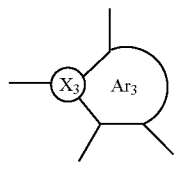
can be phenyl or pyridine.
In one aspect,
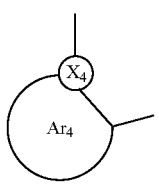
can be phenyl, pyridine, isoquinoline, naphthyl,
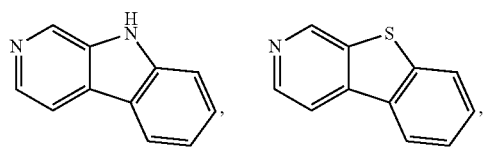
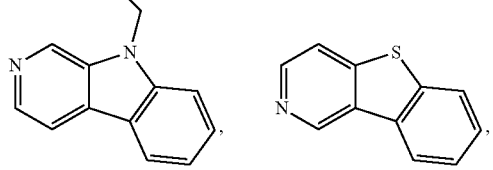
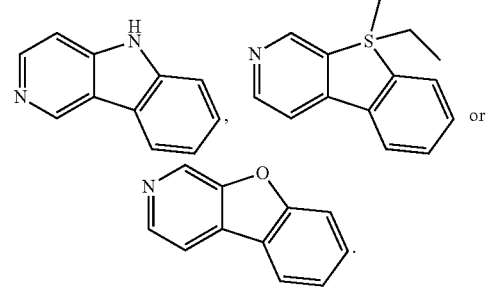
For example,
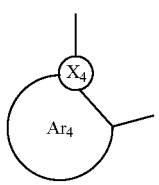
can be phenyl. In another example,
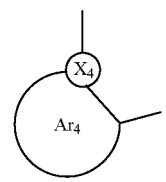
can be pyridine. In another example,
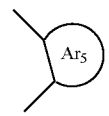
can be naphthyl or isoquinoline.
In one aspect,
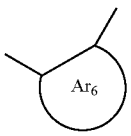
can be phenyl.
In one aspect,
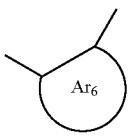
can be phenyl or absent. For example,
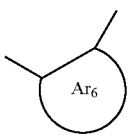
can be absent. In another example,
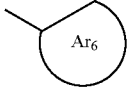
can be phenyl.

In one aspect,

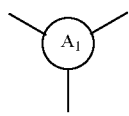

can be

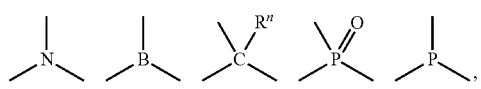

or a combination thereof. In one aspect, $R''$ can be $C_1$-$C_6$ alkyl, such as $C_2$ alkyl. For example,

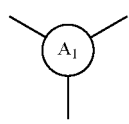

can be

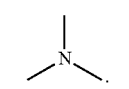

In one aspect,

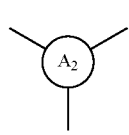

can be

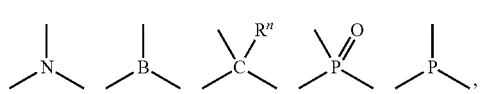

or a combination thereof. In one aspect, $R''$ can be $C_1$-$C_6$ alkyl, such as $C_2$ alkyl. For example,

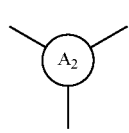

can be

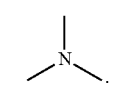

In another aspect,

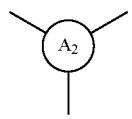

can be —O—, if

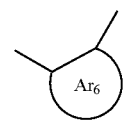

is absent.
In one aspect,

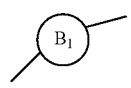

can be present or absent. For example,

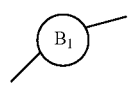

can be absent. If present,

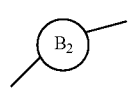

can be —O—.
In one aspect, can be present or absent. For example, can be absent. In another example, can be —S—, —S($R^1$)$_2$—, —C($R^2$)$_2$—, —O—, —NH— or —NR''—. In one aspect, each $R^1$ can individually be H or $C_1$-$C_3$ alkyl, for example $C_2$ alkyl. In one aspect, each $R^2$ can individually be H or $C_1$-$C_3$ alkyl, for example $C_1$ alkyl. In one aspect, $R''$ can be $C_1$-$C_3$ alkyl. For example, $R''$ can be $C_2$ alkyl.

In one aspect,

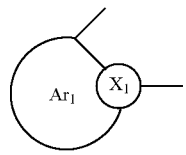

can be pyridine, isoquinoline, methylimidazole, or

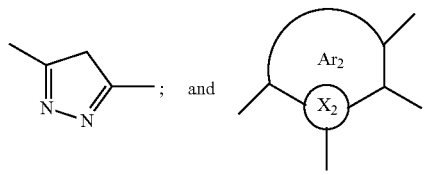

can be phenyl. In another aspect,

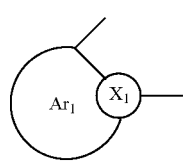

can be pyridine, isoquinoline, methylimidazole, or

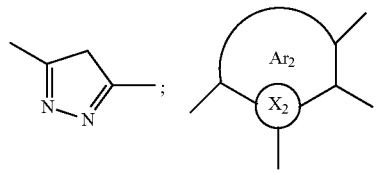

can be phenyl; and

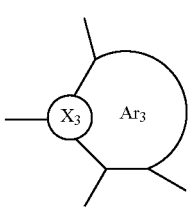

can be pyridine. In another aspect,

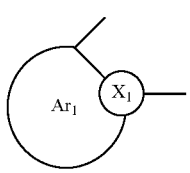

can be pyridine, isoquinoline, methylimidazole, or

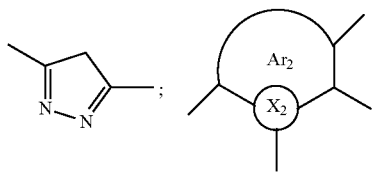

can be phenyl; and

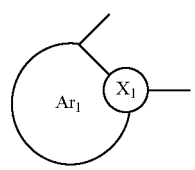

can be phenyl. In another aspect,

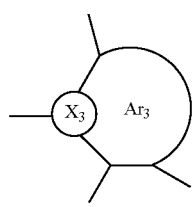

can be pyridine, isoquinoline, methylimidazole, or

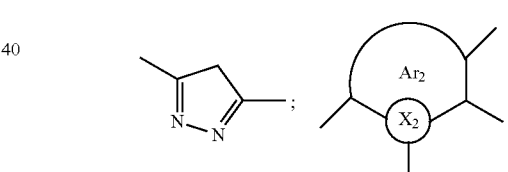

can be phenyl;

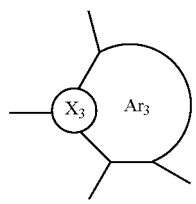

can be pyridine or phenyl;

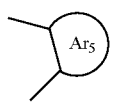

can be phenyl; and

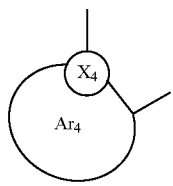

can be phenyl or pyridine. In another aspect,

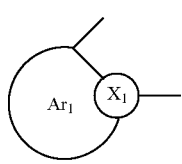

can be pyridine, isoquinoline, methylimidazole, or

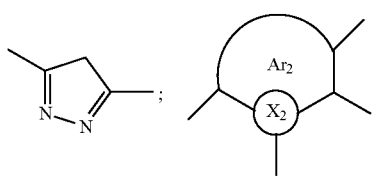

can be phenyl;

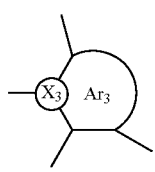

can be pyridine or phenyl; and

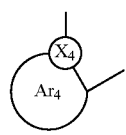

can be phenyl or pyridine;

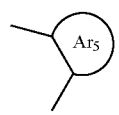

can be phenyl; and

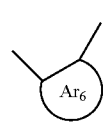

can be absent. In another aspect,

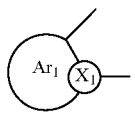

can be pyridine, isoquinoline, methylimidazole, or

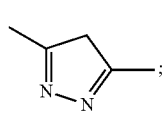 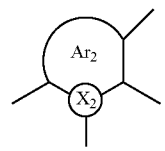

can be phenyl;

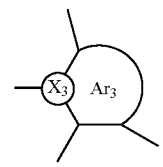

can be pyridine or phenyl; and

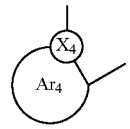

can be phenyl or pyridine;

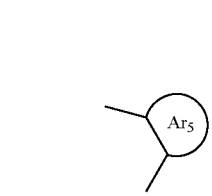

can be phenyl; and

can be phenyl.

In yet another aspect, the compositions of the present invention can be represented by the general formula:

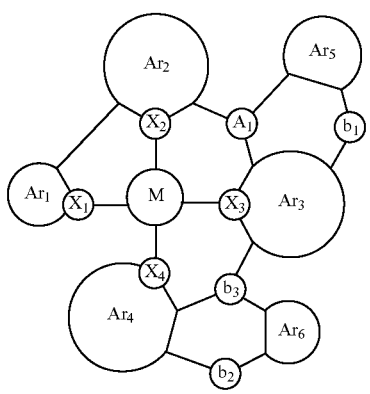

wherein M represents platinum, palladium, or a combination thereof, wherein each of $Ar_1$, $Ar_2$, $Ar_3$, and $Ar_4$ independently represent an aromatic ring or heterocyclic group which can be substituted or unsubstituted; wherein each of $X_1$, $X_2$, $X_3$ and $X_4$ can individually be coordinated to the platinum and/or palladium atom, and can independently represent a carbon and/or a nitrogen atom, wherein $Ar_5$ can represent an aromatic ring, a heterocyclic group, or a combination thereof, wherein $Ar_6$ can represent an aromatic ring, a heterocyclic group, a combination thereof, or can be absent; wherein $A_1$ can represent a linking atom, such as, for example, nitrogen, carbon, boron, phosphorus, silicon, or a combination thereof, and wherein $A_1$ can optionally be substituted, wherein each $b_1$, $b_2$, and $b_3$ can individually optionally be present or absent, and if present can independently represent oxygen, sulfur, nitrogen, carbon, boron, phosphorus, silicon, or a combination thereof.

In one aspect, M can be Pt, such as Pt(II). In another aspect, M can be Pd, such as Pd(II).

In one aspect,

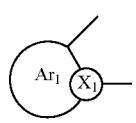

can be pyridine, quinazoline, isoquinoline, methylimidazole, or

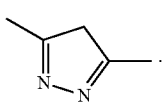

In one aspect,

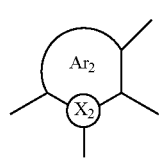

can be phenyl or pyridine.

In one aspect,

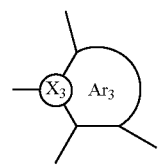

can be phenyl or pyridine.

In one aspect,

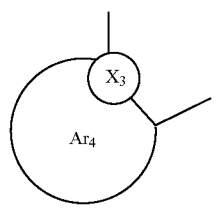

can be phenyl, pyridine, isoquinoline, naphthyl,

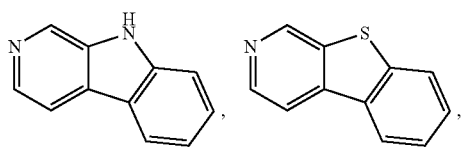

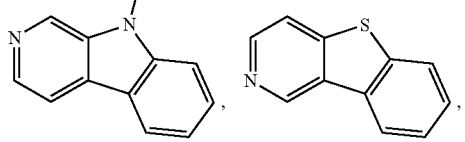

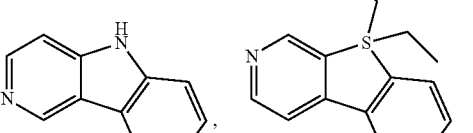

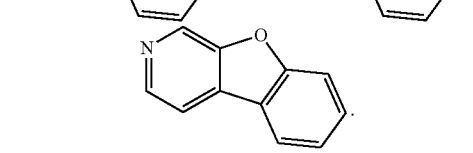

For example,

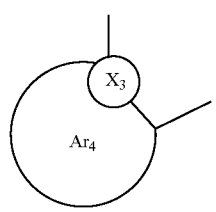

can be phenyl. In another example,

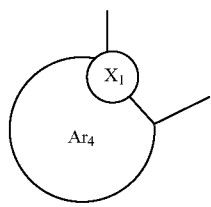

can be pyridine. In another example,

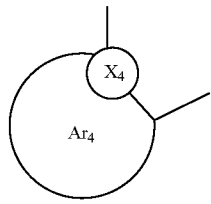

can be naphthyl or isoquinoline.

In one aspect,

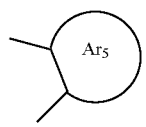

can be phenyl.

In one aspect,

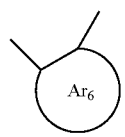

can be phenyl or absent. For example,

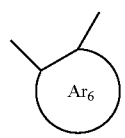

can be absent. In another example,

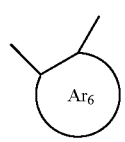

can be phenyl.

In one aspect,

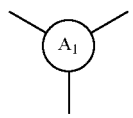

can be

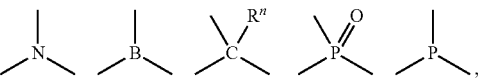

or a combination thereof. In one aspect, $R''$ can be $C_1$-$C_6$ alkyl, such as $C_2$ alkyl. For example,

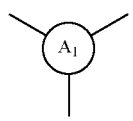

can be

In one aspect,

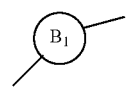

can be present or absent. For example,

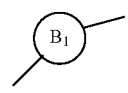

can be absent. If present,

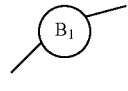

can be —O—.

In one aspect,

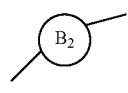

can be present or absent. For example,

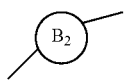

can be absent. In another example,

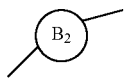

can be —S—, —S(R$^1$)$_2$—, —C(R$^2$)$_2$—, —O—, —NH— or —NR″—. In one aspect, each R$^1$ can individually be H or C$_1$-C$_3$ alkyl, for example C$_2$ alkyl. In one aspect, each R$^2$ can individually be H or C$_1$-C$_3$ alkyl, for example C$_1$ alkyl. In one aspect, R″ can be C$_1$-C$_3$ alkyl. For example, R″ can be C$_2$ alkyl.

In one aspect,

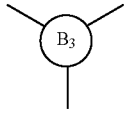

can be

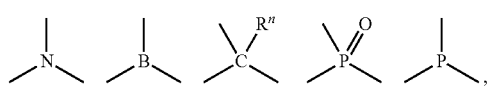

or a combination thereof. In one aspect, R″ can be C$_1$-C$_6$ alkyl, such as C$_2$ alkyl. For example,

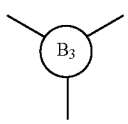

can be

In one aspect,

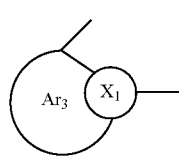

can be pyridine, isoquinoline, methylimidazole, or

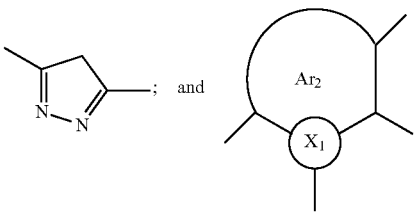

can be phenyl. In another aspect,

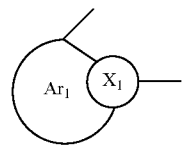

can be isoquinoline, methylimidazole, or

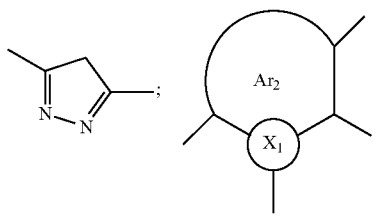

can be phenyl; and

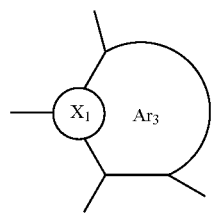

can be pyridine. In another aspect,

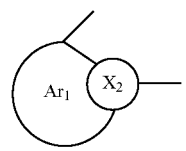

can be isoquinoline, methylimidazole, or

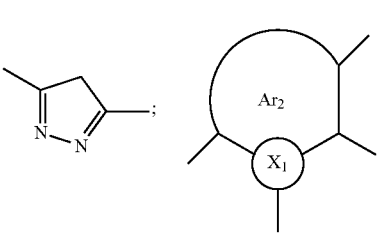

can be phenyl; and

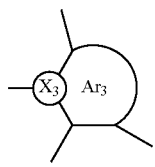

can be phenyl. In another aspect,

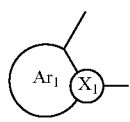

can be isoquinoline, methylimidazole, or

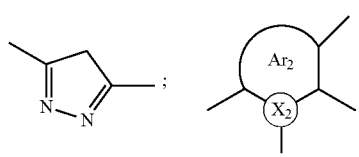

can be phenyl;

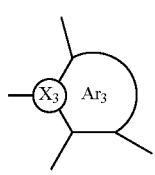

can be pyridine or phenyl; and

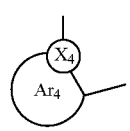

can be phenyl or pyridine. In another aspect,

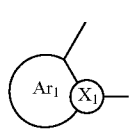

can be isoquinoline, methylimidazole, or

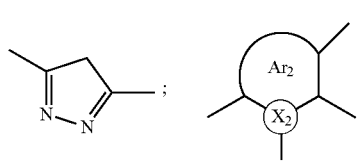

can be phenyl;

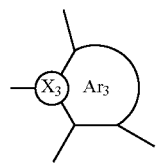

can be pyridine or phenyl; and

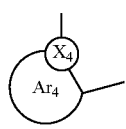

can be phenyl or pyridine; and

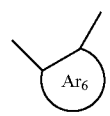

can be absent. In another aspect,

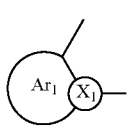

can be isoquinoline, methylimidazole, or

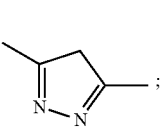

can be phenyl;

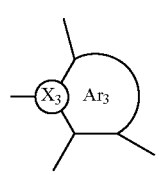

can be pyridine or phenyl; and

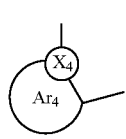

can be phenyl or pyridine; and
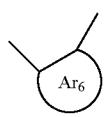
can be phenyl.
In one aspect, each of the above formulas
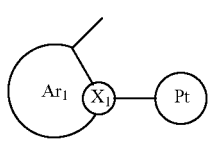
can comprise one or more of the following:
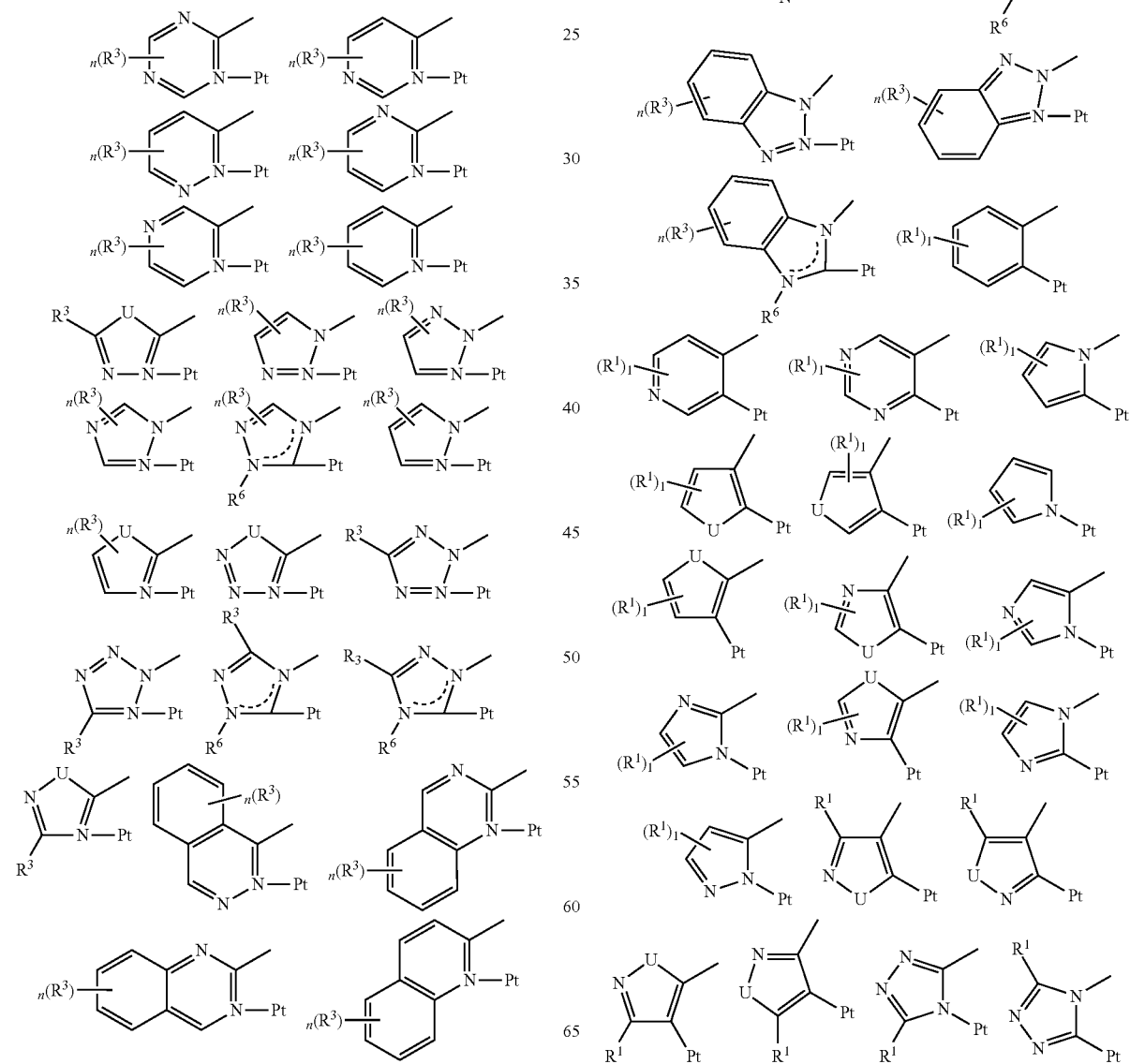

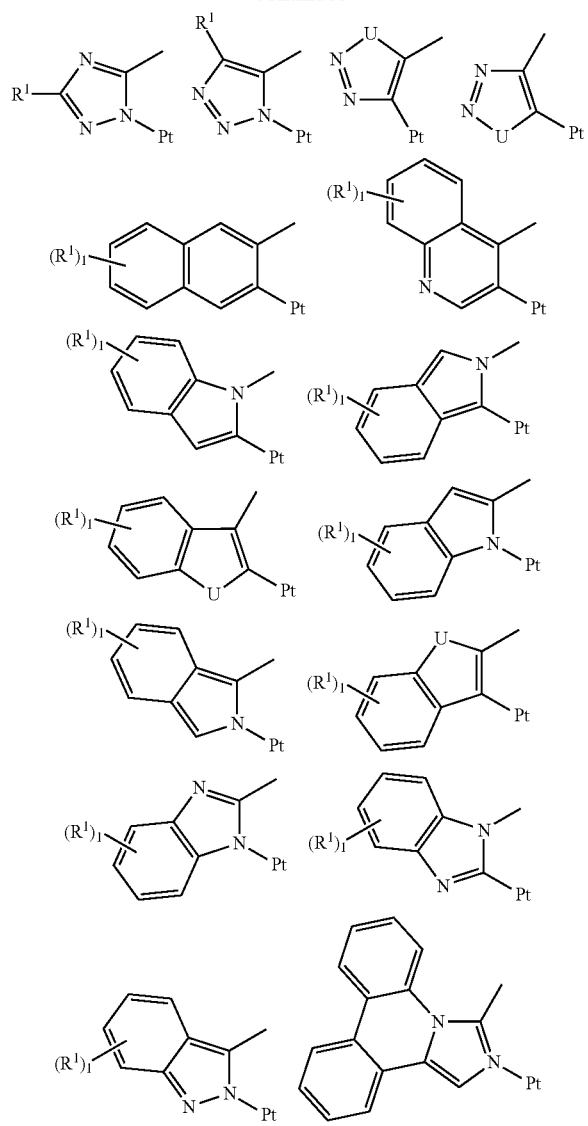

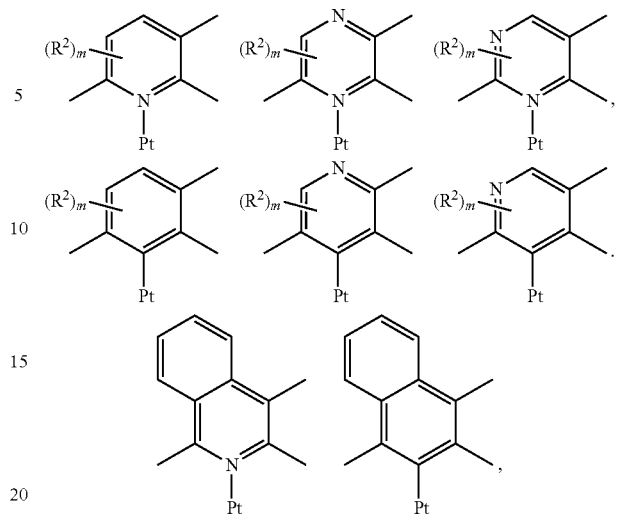

or a combination thereof. In one aspect, m can be 1 or 0. In one aspect, $R^2$ can be $C_1$-$C_3$ alkyl, for example $C_2$ alkyl.

In another aspect, in all above formulas each

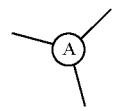

can independently represent one or more of the following:

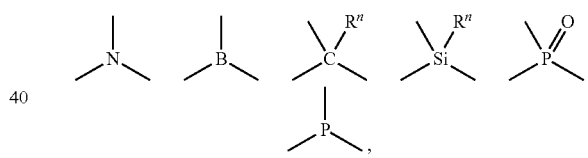

or a combination thereof. In one aspect, $R^n$ can be $C_1$-$C_3$ alkyl, such as $C_2$ alkyl.

In another aspect, in all above formulas each

can independently represent one or more of the following:

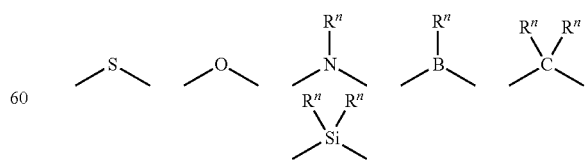

null, or a combination thereof. $B_n$ is a generic description of $B_1$, $B_2$ and/or $B_3$. In one aspect, $R''$ can be $C_1$-$C_3$ alkyl, such as $C_2$ alkyl. $B_n$ can be present or absent.

or a combination thereof. In one aspect, $R^1$ can be H or $C_1$-$C_3$ alkyl. In one aspect, n can be 1 or 0. For example, n can be 0. In one aspect, $R^3$ can be $C_1$-$C_3$ alkyl. In one aspect, U can be —C($R^2$)$_2$, —O— or —S—. Each $R^2$ can individually be H or $C_1$-$C_3$ alkyl.

In another aspect, each of the above formulas

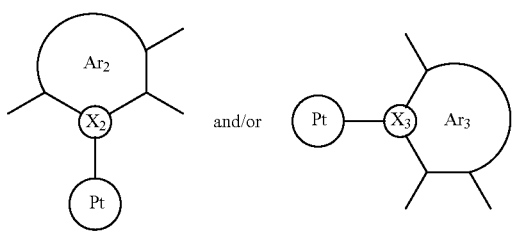

can each independently represent one or more of the following:

35
In another aspect, in all above formulas
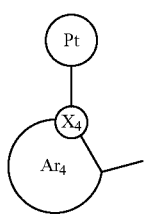
can represent one or more of the following:
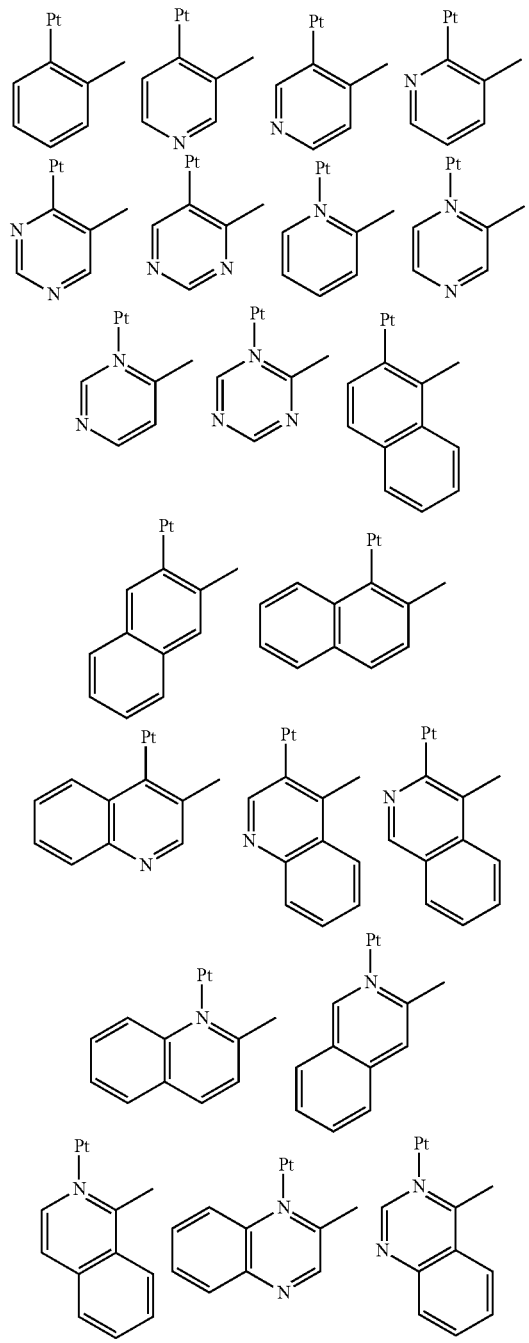
36
-continued
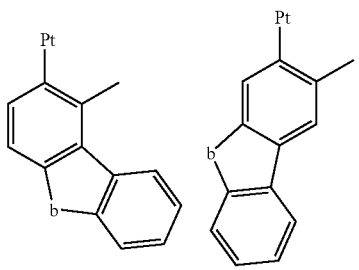
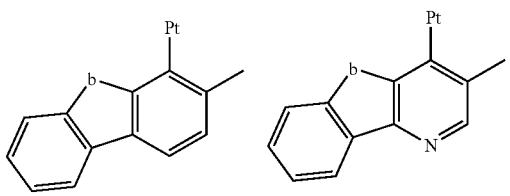
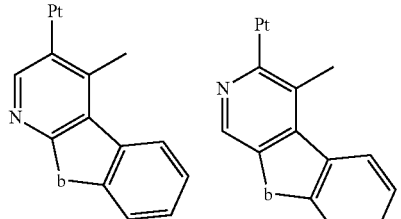
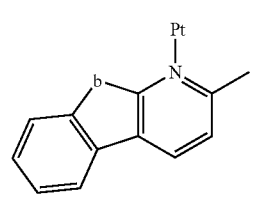
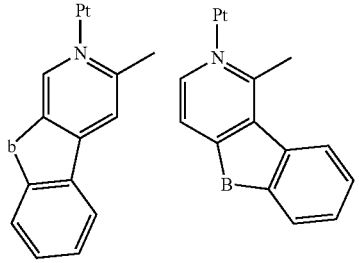
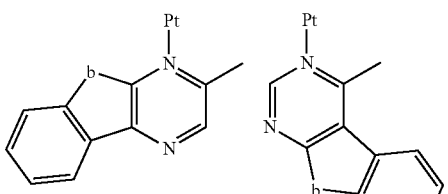
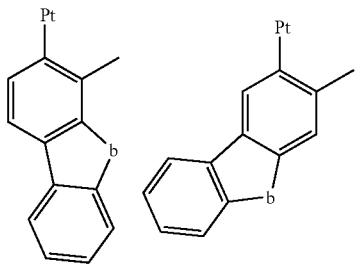

-continued

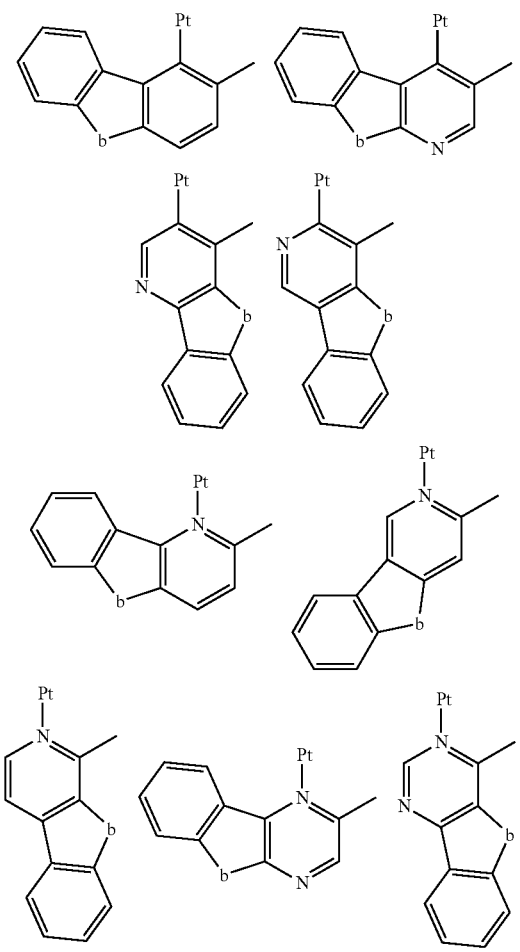

or a combination thereof. In one aspect, b can —O—, —S—, —N(R$^1$)—, or —C(R$^1$)$_2$—. In one aspect, each R$^1$ can individually be H or C$_1$-C$_3$ alkyl, such as C$_2$ alkyl. For example, b can be —O—, —S—, or —N(C$_2$H$_5$)—.

In another aspect, in all above formulas each of

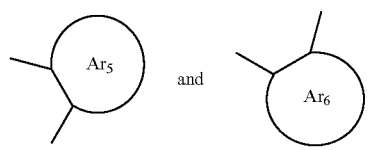

each represent one or more of the following:

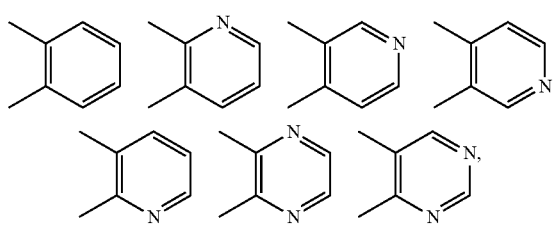

or a combination thereof. For example,

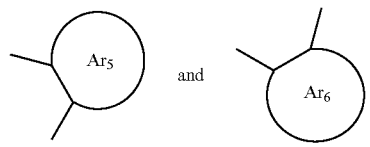

can individually be

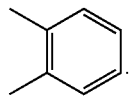

In another aspect, in all above formulas

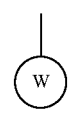

may be any one as following:

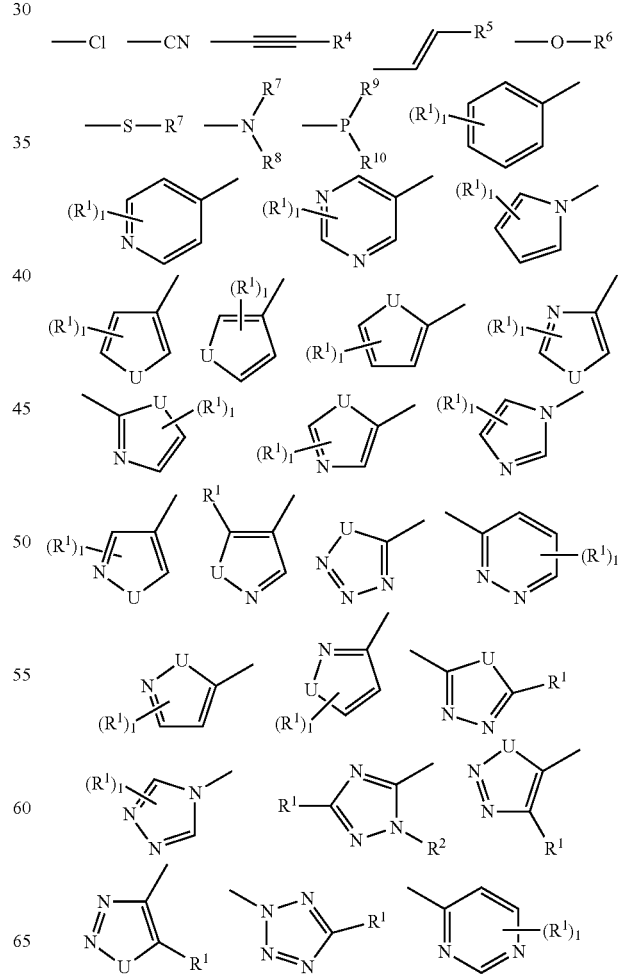

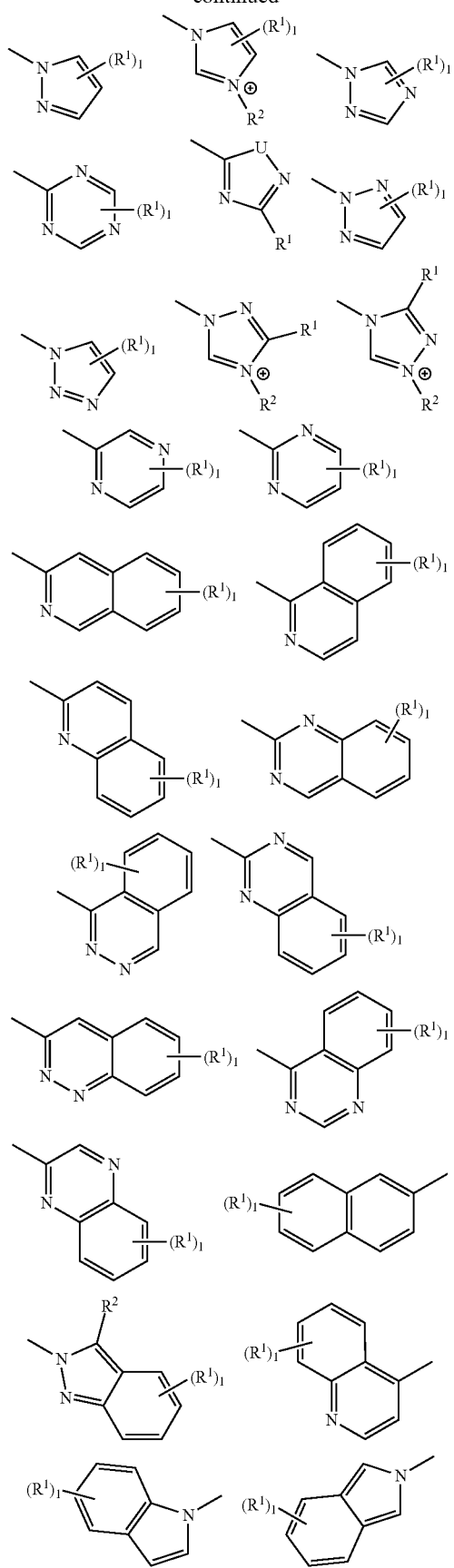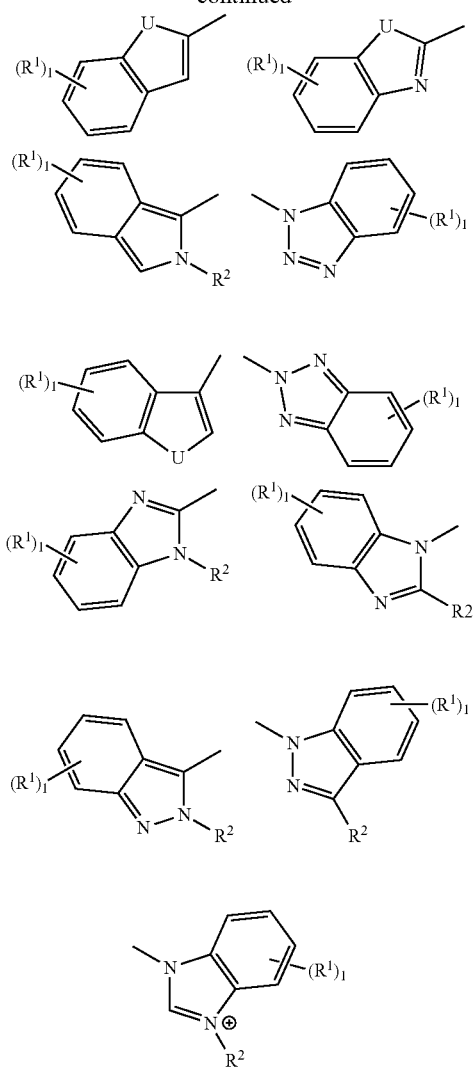

In one aspect, $R^1$, $R^2$, $R^3$, $R^4$, $R^5$, $R^6$, $R^7$, $R^8$, $R^9$, and $R^{10}$, can individually be H or $C_1$-$C_3$ alkyl, such as $C_2$ alkyl. In one aspect, $R^1$, $R^2$, $R^3$, $R^4$, $R^5$, $R^6$, $R^7$, $R^8$, $R^9$, and $R^{10}$, can individually be H. In one aspect, U can be —$C(R^2)_2$, —O— or —S—. Each $R^2$ can individually be H or $C_1$-$C_3$ alkyl.

In other aspects, the inventive composition can comprise any one or more of the following specific examples:

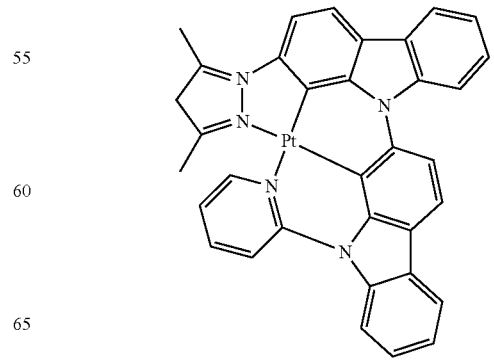

-continued
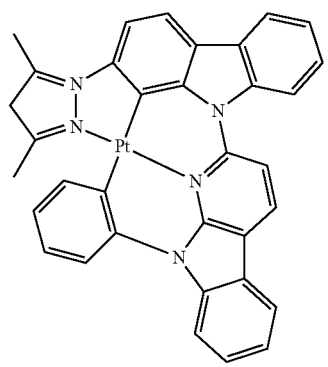
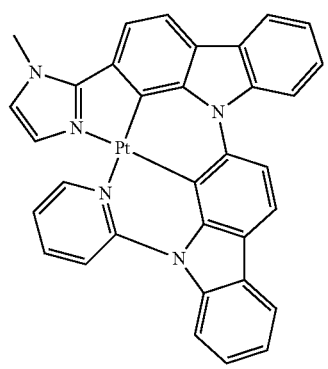
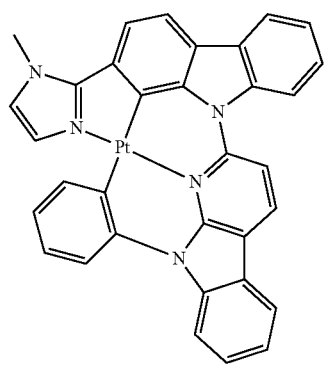
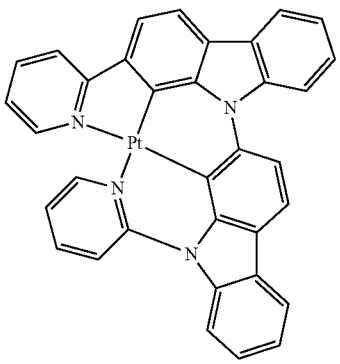
-continued
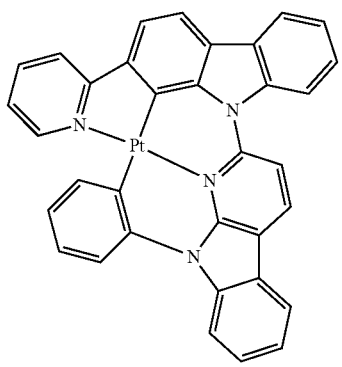
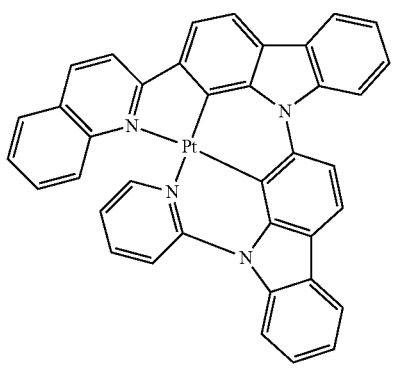
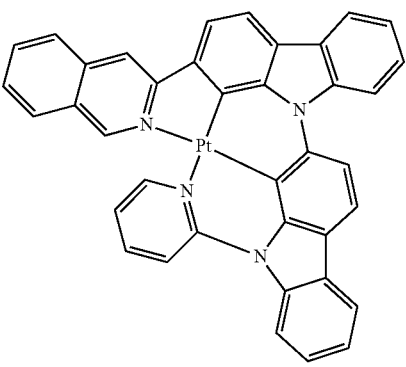
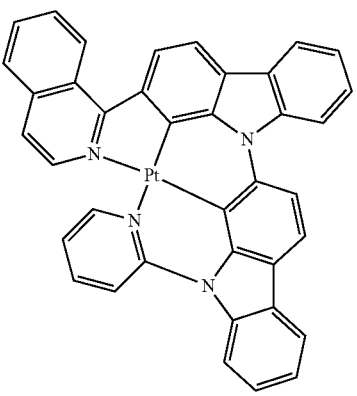

43
-continued
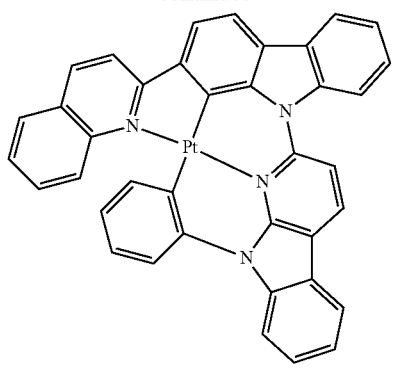
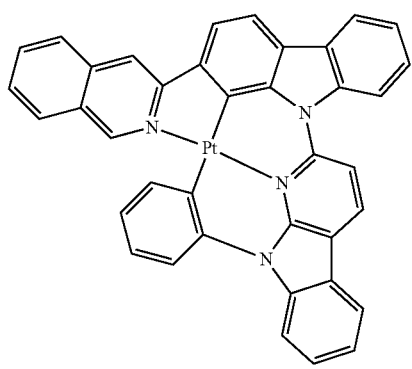
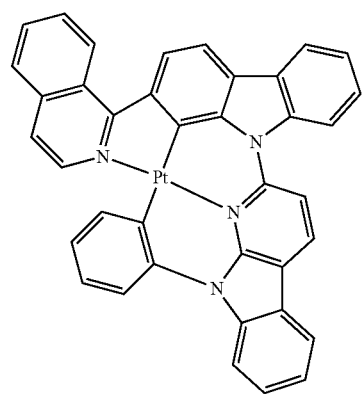
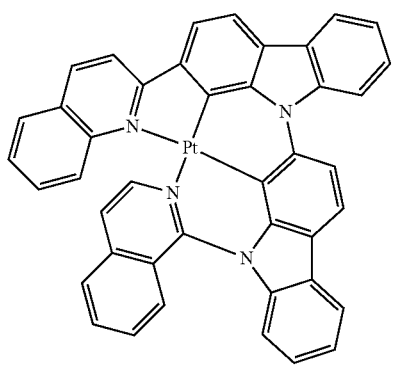
44
-continued
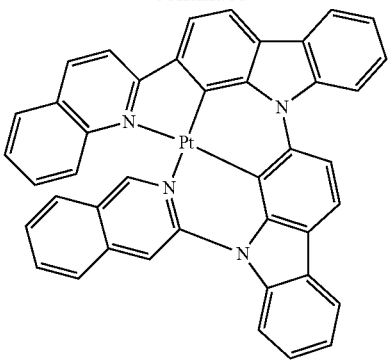
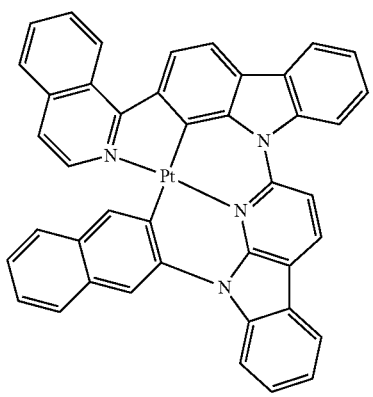
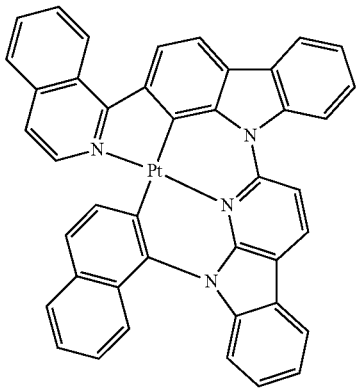
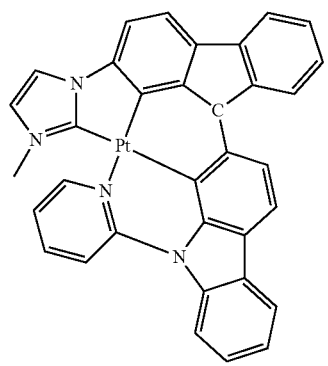

45
-continued
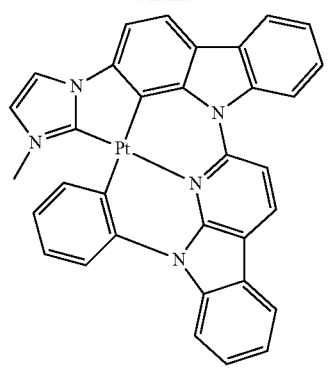
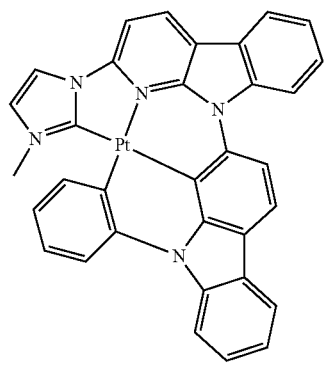
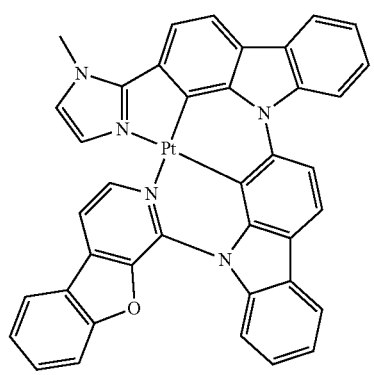
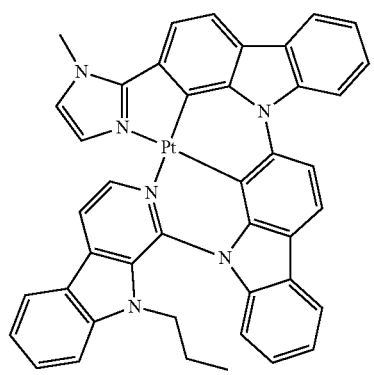
46
-continued
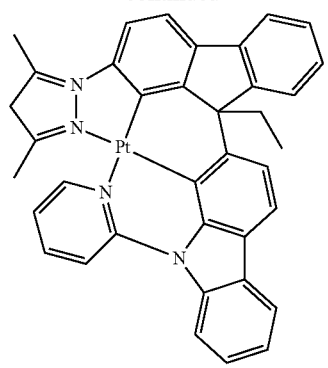
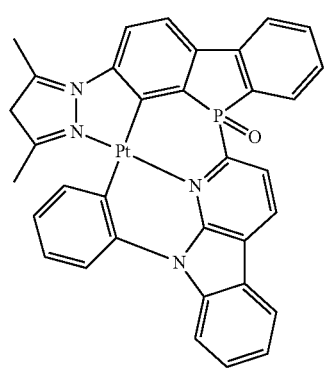
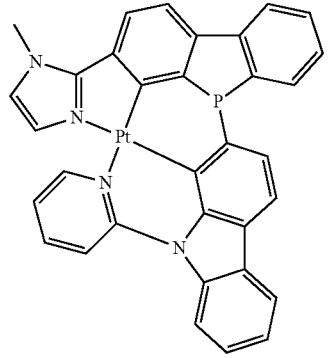
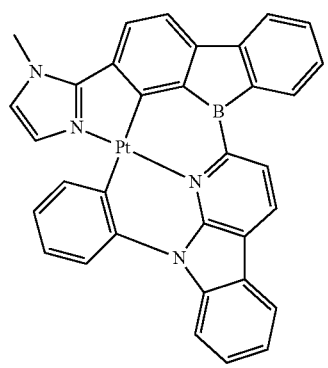

-continued
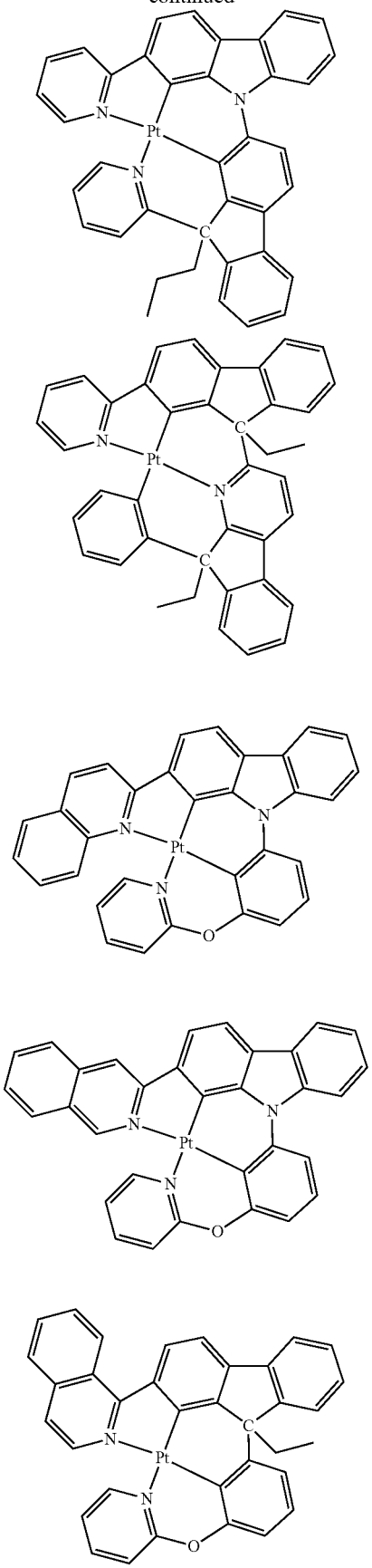
-continued
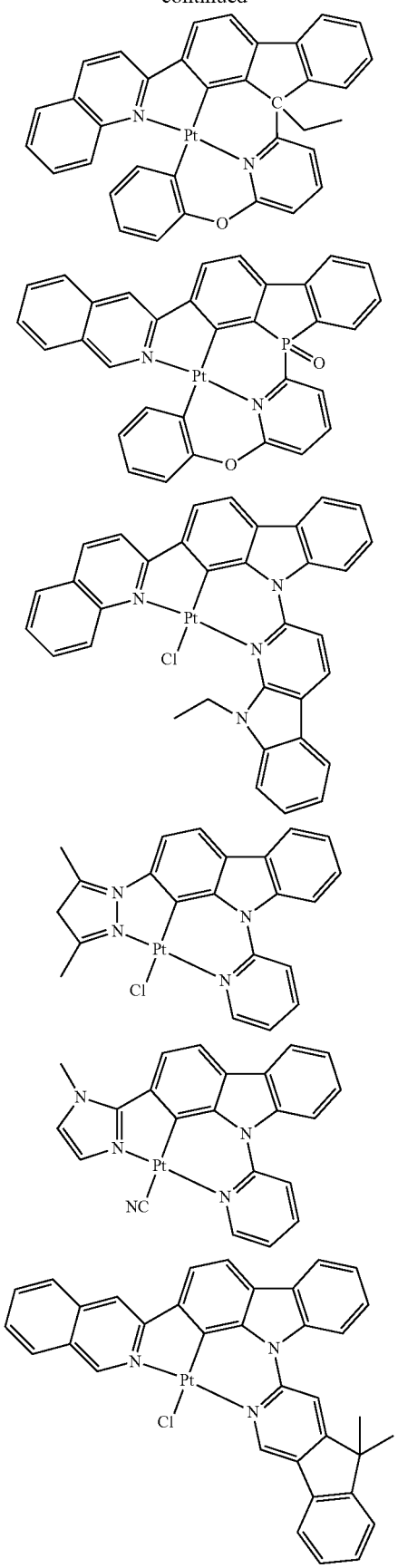

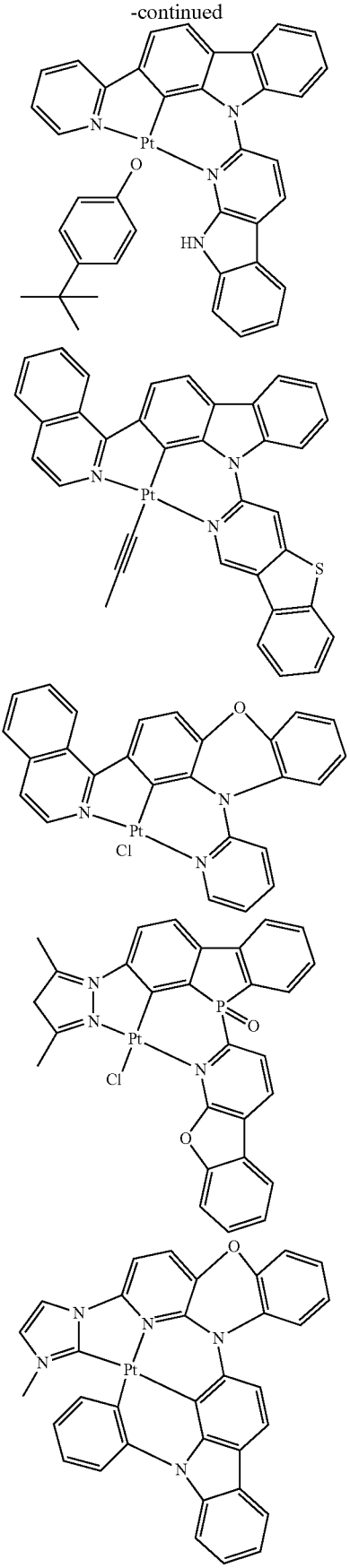
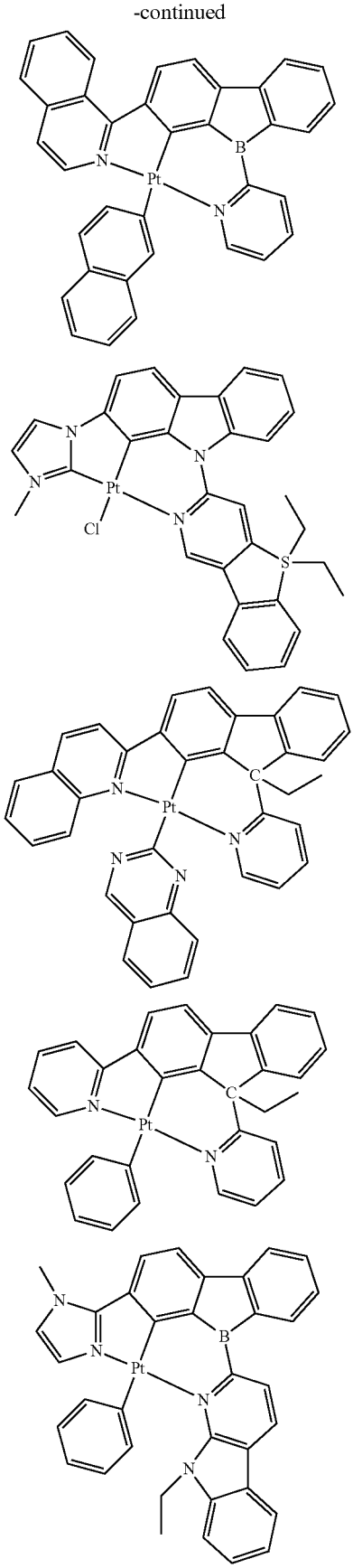

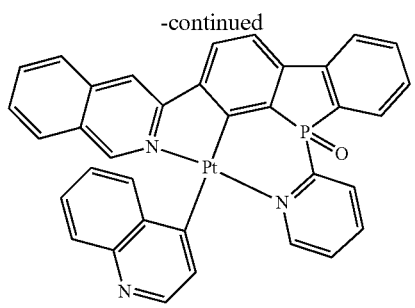

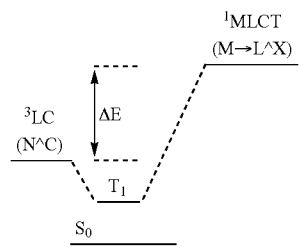

or a combination thereof.

It should be understood that the specific exemplary compositions recited herein are intended to be exemplary and not limiting. In another aspect, the present invention can exclude, or not include, any one or more of the compounds recited herein. For example, in one aspect, the present invention does not comprise the following complex:

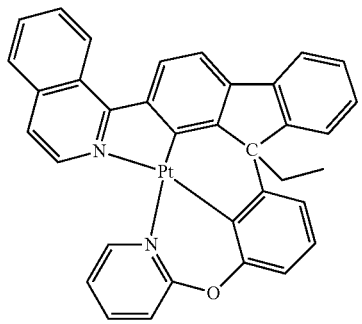

The inventive compositions of the present disclosure can be useful in a wide variety of applications, such as, for example, lighting devices. In a particular aspect, one or more of the complexes can be useful as an emitter for an organic light emitting display device.

The compounds of the invention are useful in a variety of applications. As light emitting materials, the compounds can be useful in organic light emitting diodes (OLEDs), luminescent devices and displays, and other light emitting devices, or as luminescent markers in bio-applications.

The emission (and absorption) profile of the compounds can be tuned by varying the structure of the ligand surrounding the metal center. For example, compounds having a ligand with electron withdrawing substituents will generally exhibit different optical properties, including emission and absorption, than compounds having a ligand with electron donating substituents. Generally, a chemical structural change affects the electronic structure of the compound, which thereby affects the absorption and emission of the compound. Thus, the compounds of the present invention can be tailored or tuned to a specific application that desires a particular emission or absorption characteristic.

In another aspect, the emission spectrum of any of the compositions of the present disclosure can be tuned to a desired and/or customized spectrum. In another aspect, the complexes disclosed herein can provide a narrow bandwidth, enabling their use in, for example, applications in which broad spectrum emitters are not suitable.

In one aspect, the excited state dynamics of the complex can be described by the scheme:

where $^3LC$ represents the energy of the ligand centered triplet state, $^1MLCT$ represents the energy of the metal-to-ligand charge transfer singlet state, $T_1$ represents the energy of the emissive triplet state, $S_0$ represents the energy of the ground state, and $\Delta E$ represents the difference in energy between $^1MLCT$ and $^3LC$.

In still another aspect, an expansion utilizing different emitting portions and linking groups should provide narrow emitting complexes covering a wide range of the visible spectrum. The emission energy of a certain complex can be tuned by modifying the ligand centered triplet state of the emitting fragment ($^3LC$). This can be accomplished through changes in structure that modify the energy of the donating or accepting portion of the emitting fragment.

In another aspect, the nature of the $^1MLCT$ transitions can be controlled by modifying the ancillary portion of the complex ($L^X$), through changes in the cyclometalating portion, the linking portions, or both.

In one aspect, the inventive compositions are useful as emitters for full color display application. In such an aspect, the geometry of cyclometalating ligands can be rigid. This rigidity can allow for similar geometry between the ground and excited state, resulting in a narrow emission spectra dominated by the transition from the lowest vibrational level in the excited state to the lowest vibrational level in the ground state.

In another aspect, complexes can be designed to tune the values of the emitting fragment centered $^3LC$ state and the metal to ancillary ligand $^1MLCT$ states independently. Reduction in the differences in energy between these states ($\Delta E$) will improve mixing between them, improve the radiative decay rate, and suppress transitions that occur from the emissive state ($T_1$) to excited vibrational levels in the ground state ($S_0$). As a consequence, the vibrational shoulders of the emission spectra can be reduced, resulting in a more narrow emission profile.

In a further aspect, the molecular structure having four coordinating ligands to a metal center can be preferred. In such an aspect, a four ligand coordinated structure can at least partially ensure the electrochemical and/or photophysical stability of the complex during, for example, fabrication and operation of a color display device.

In another aspect, the inventive compositions can provide improved efficiency and/or operational lifetimes in lighting devices, such as, for example, organic light emitting devices, such as OLEDs, as compared to conventional materials. Thus, also disclosed herein are devices comprising the complexes described herein. One application for phosphorescent emissive complexes, such as those described herein, is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

In other various aspects, the inventive compositions can be useful as, for example, luminescent labels, emitters for organic light emitting diodes, lighting applications, and combinations thereof.

The compounds of the invention can be made using a variety of methods, including, but not limited to those recited in the examples provided herein. In other aspects, one of skill in the art, in possession of this disclosure, could readily determine an appropriate method for the preparation of an iridium complex as recited herein.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

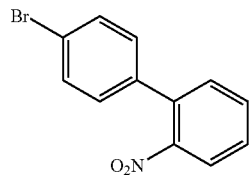

4'-bromo-2-nitrobiphenyl: Under a nitrogen atmosphere, 20 mL of water was heated to 60° C. and 125 mmol of 2-nitrobyphenyl was added and stirred for 30 minutes before 6.3 mmol of iron trichloride was added and stirred for 30 minutes further. 140 mmol of bromine was added dropwise over 40 minutes and allowed to stir overnight before setting to reflux for 4 hours. After cooling, residual bromine was removed by washing with a sodium bisulfate solution. The organic residue was then washed twice with water, twice with concentrated sodium hydroxide, and then twice with water. The organic portion was separated and dissolved in dichloromethane before being dried with magnesium sulfate. The solution was concentrated under reduced pressure, subjected to flash column chromatography of silica with dichloromethane as the eluent, and concentrated again under reduced pressure. 4'-bromo-2-nitrobiphenyl was collected by recrystallization from methanol in 50% yield.

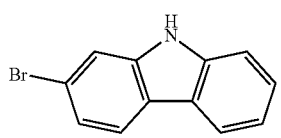 [SMILES: Brc1ccc2c(c1)[nH]c1ccccc12]

2-bromo-9H-carbazole: Under a nitrogen atmosphere, 100 mmol of 4'-bromo-2-nitrobiphenyl was set to reflux overnight in stirring triethylphosphite. After cooling, the triethylphosphite was distilled off and 2-bromo-9H-carbazole was isolated by recrystallization from methanol and further purified by train sublimation, resulting in a 65% yield.

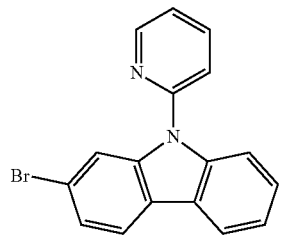 [SMILES: Brc1ccc2c3ccccc3n(-c3ccccn3)c2c1]

2-bromo-9-(pyridin-2-yl)-9H-carbazole: Under a nitrogen atmosphere, 10 mmol of 2-bromo-9H-carbazole, 15 mmol of 2-bromopyridine, 1 mmol of copper(I)iodide, 25 mmol of potassium carbonate, and 2 mmol of L-proline were combined in stirring degassed dimethyl sulfoxide. The mixture was heated to 90° C. for 3 days before being cooled and separated between dichloromethane and water. The water layer was washed twice with dichloromethane and the organics were combined and washed once with brine. The organic fraction was dried with magnesium sulfate and concentrated under reduced pressure and subjected to column chromatography of silica with dichloromethane as the eluent. After concentrating under reduced pressure, 2-bromo-9-(pyridin-2-yl)-9H-carbazole was isolated in a 70% yield.

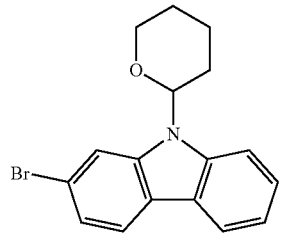 [SMILES: Brc1ccc2c3ccccc3n(C3CCCCO3)c2c1]

2-bromo-9-(tetrahydro-2H-pyran-2-yl)-9H-carbazole: 10 mmol of 2-bromo-9H-carbazole, 0.1 mmol of pyridinium toluene-4-sulphonate, and 50 mmol of 3,4-dihydro-2H-pyran was added to dichloromethane at room temperature and let stir for 2 hours before the temperature was raised to 50° C. for 2 hours further. The solution was cooled, concentrated under reduced pressure, and subjected to column chromatography of silica with dichloromethane as the eluent. After concentrating under reduced pressure, 2-bromo-9-(tetrahydro-2H-pyran-2-yl)-9H-carbazole was isolated in 90% yield.

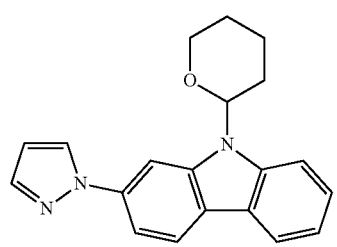 [SMILES: c1ccc2c(c1)c1ccc(-n3cccn3)cc1n2C1CCCCO1]

2-(1H-pyrazol-1-yl)-9-(tetrahydro-2H-pyran-2-yl)-9H-carbazole: Under a nitrogen atmosphere, 10 mmol of 2-bromo-9-(tetrahydro-2H-pyran-2-yl)-9H-carbazole, 15 mmol of pyrazole, 1 mmol of copper(I)iodide, 25 mmol of potassium carbonate, and 2 mmol of L-proline were combined in 25 mL of stirring degassed dimethyl sulfoxide. The mixture was heated to 90° C. for 3 days before being cooled and separated between dichloromethane and water. The water layer was washed twice with dichloromethane and the organics were combined and washed once with brine. The organic fraction was dried with magnesium sulfate and concentrated under reduced pressure and subjected to column chromatography of silica with dichloromethane as the eluent. After concentrating under reduced pressure, 2-(1H-pyrazol-1-yl)-9-(tetrahydro-2H-pyran-2-yl)-9H-carbazole was isolated in a 40% yield.

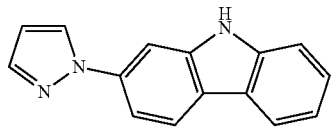 [SMILES: c1ccc2c(c1)[nH]c1cc(-n3cccn3)ccc12]

2-(1H-pyrazol-1-yl)-9H-carbazole: 5 mmol of 2-(1H-pyrazol-1-yl)-9-(tetrahydro-2H-pyran-2-yl)-9H-carbazole was dissolved in 100 mL of methanol before 25 mmol of methylsulfonic acid was added slowly. The solution was stirred at room temperature for 2 hours, then at 50° C. for 2 hours further. The reaction was cooled, quenched with sodium bicarbonate, and separated between dichloromethane and water. The water was washed twice with dichloromethane, the organic fractions combined and washed once with brine. The organic fraction was then dried with magnesium sulfate, filtered, and the filtrate concentrated under reduced pressure. The resulting solid was subjected to column chromatography, using silica and dichloromethane/ethyl acetate as the eluent. After concentration under reduced pressure, 2-(1H-pyrazol-1-yl)-9H-carbazole was isolated in 90% yield.

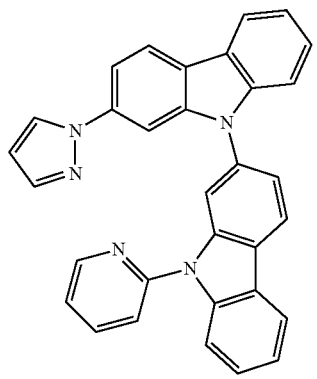 [SMILES: c1ccc(-n2c3ccccc3c3ccc(-n4c5ccccc5c5ccc(-n6cccn6)cc54)cc32)nc1]

2'-(1H-pyrazol-1-yl)-9-(pyridin-2-yl)-9H-2,9'-bicarbazole: Under a nitrogen atmosphere, 10 mmol of 2-(1H-pyrazol-1-yl)-9H-carbazole, 10 mmol of 2-bromo-9-(pyridin-2-yl)-9H-carbazole, 1 mmol of copper(I)iodide, 25 mmol of potassium carbonate, and 2 mmol of L-proline were combined in stirring degassed dimethyl sulfoxide. The mixture was heated to 90° C. for 3 days before being cooled and separated between dichloromethane and water. The water layer was washed twice with dichloromethane and the organics were combined and washed once with brine. The organic fraction was dried with magnesium sulfate and concentrated under reduced pressure and subjected to column chromatography of silica with dichloromethane/ethyl acetate as the eluent. After concentrating under reduced pressure, 2'-(1H-pyrazol-1-yl)-9-(pyridin-2-yl)-9H-2,9'-bicarbazole was isolated in a 60% yield.

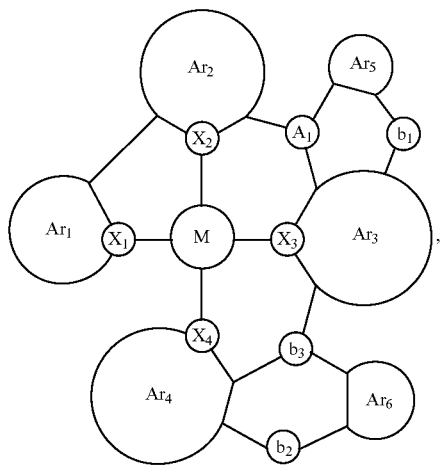

[2'-(1H-pyrazol-1-yl)-9-(pyridin-2-yl)-9H-2,9'-bicarbazole]Pt(II), PtN1N: Under a nitrogen atmosphere, 10 mmol of 2'-(1H-pyrazol-1-yl)-9-(pyridin-2-yl)-9H-2,9'-bicarbazole, 9 mmol of $K_2PtCl_4$, and 4Å molecular sieves were added to stirring acetic acid. The mixture was heated to 120° C. for 3 days. The solution was cooled, and poured into 100 mL of stirring dichloromethane. The mixture was filtered, and the filtrate concentrated under reduced pressure. The emissive solid was subjected to flash chromatography of silica with dichloromethane as the eluent.

What is claimed is:
1. A composition comprising a complex of the formula:

wherein:
  M is platinum or palladium,
  $Ar_1$ is substituted or unsubstituted: pyridyl, quinazolinyl, isoquinolinyl, imidazolyl, pyrazolyl, or benzimidazolyl,
  each $Ar_2$, $Ar_3$, and $Ar_4$ is substituted or unsubstituted: phenyl or pyridyl,
  each of $X_1$, $X_2$, $X_3$, and $X_4$ is independently a carbon or a nitrogen atom, Ar₅ is substituted or unsubstituted phenyl,
Ar₆ is substituted or unsubstituted phenyl or is absent,
A₁ is an optionally substituted nitrogen, carbon, boron, phosphorus, or silicon atom,
each of b₁, b₂, and b₃ is individually present or absent, and each b₁, b₂, and b₃ present is independently an oxygen, sulfur, or optionally substituted: nitrogen, carbon, boron, phosphorus, or silicon atom.

2. The composition of claim 1, wherein

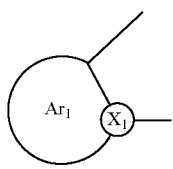

is isoquinolinyl, methylimidazolyl, or

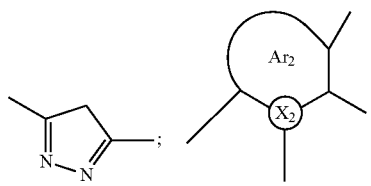

is phenyl;

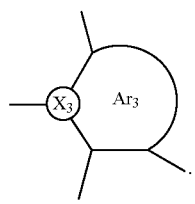

is pyridyl or phenyl;

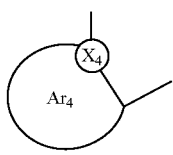

is phenyl or pyridyl;

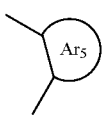

is: phenyl; and

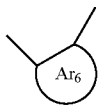

is absent.

3. The composition of claim 1, wherein the complex is represented by the structure:

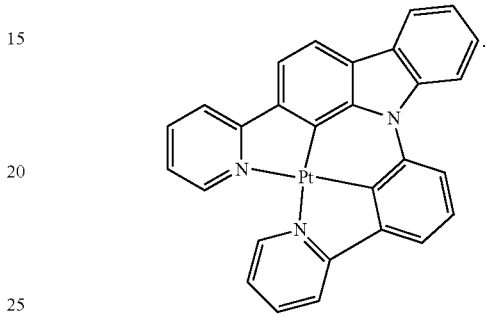

4. The complex of claim 1.
5. A light-emitting device comprising the complex of claim 1.
6. A lighting device comprising the light-emitting device of claim 5.
7. The lighting device of claim 6, wherein the lighting device comprises a full color display.
8. The complex of claim 3.
9. A light-emitting device comprising the complex of claim 8.
10. A lighting device comprising the light-emitting device of claim 9.
11. The lighting device of claim 10, wherein the lighting device comprises a full color display.
12. The composition of claim 1, wherein Ar₁ is substituted or unsubstituted: pyridyl, imidazolyl, or pyrazolyl.
13. The composition of claim 1, wherein Ar₁ is substituted or unsubstituted pyridyl.
14. The composition of claim 1, wherein each Ar₂ and Ar₃ is substituted or unsubstituted phenyl.
15. The composition of claim 1, wherein Ar₄ is substituted or unsubstituted pyridyl.
16. The composition of claim 1, wherein each of X₁ and X₄ is nitrogen atom.
17. The composition of claim 1, wherein each of X₂ and X₃ is carbon atom.
18. The composition of claim 1, wherein Ar₆ is absent.
19. The composition of claim 1, wherein A₁ is an optionally substituted nitrogen atom.
20. The composition of claim 1, wherein b₂ is absent.
21. The composition of claim 1, wherein b₁ is absent such that Ar₅ and Ar₃ are connected through a bond; and b₃ is absent such that Ar₃ and Ar₄ are connected through a bond.

* * * * *

UNITED STATES PATENT AND TRADEMARK OFFICE
CERTIFICATE OF CORRECTION

PATENT NO. : 9,698,359 B2  
APPLICATION NO. : 14/996522  
DATED : July 4, 2017  
INVENTOR(S) : Jian Li and Eric Turner Page 1 of 1

It is certified that error appears in the above-identified patent and that said Letters Patent is hereby corrected as shown below:

In Column 57, In Line 33-40 (Approx.), In Claim 2, delete:

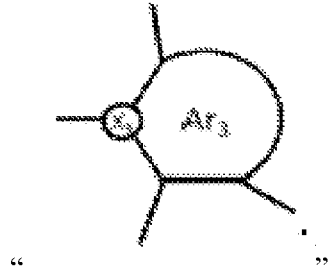

"                                "

And insert:

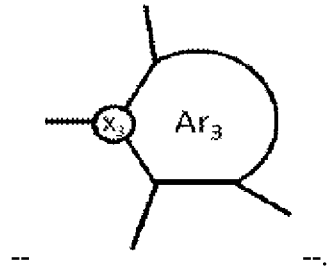

--                          --.

Signed and Sealed this  
Third Day of October, 2017

Joseph Matal  
*Performing the Functions and Duties of the*  
*Under Secretary of Commerce for Intellectual Property and*  
*Director of the United States Patent and Trademark Office*